United States Patent
Murakoshi et al.

(10) Patent No.: US 10,485,631 B2
(45) Date of Patent: Nov. 26, 2019

(54) INSERTION DEVICE AND PHOTOACOUSTIC MEASUREMENT APPARATUS

(71) Applicant: FUJIFILM Corporation, Tokyo (JP)

(72) Inventors: Dai Murakoshi, Ashigarakami-gun (JP); Kaku Irisawa, Ashigarakami-gun (JP)

(73) Assignee: FUJIFILM Corporation, Tokyo (JP)

(*) Notice: Subject to any disclaimer, the term of this patent is extended or adjusted under 35 U.S.C. 154(b) by 272 days.

(21) Appl. No.: 15/711,807

(22) Filed: Sep. 21, 2017

(65) Prior Publication Data
US 2018/0008369 A1    Jan. 11, 2018

Related U.S. Application Data

(63) Continuation of application No. PCT/JP2016/054770, filed on Feb. 19, 2016.

(30) Foreign Application Priority Data

Mar. 31, 2015 (JP) ................. 2015-071945

(51) Int. Cl.
*A61B 1/00* (2006.01)
*A61B 90/35* (2016.01)
(Continued)

(52) U.S. Cl.
CPC .......... *A61B 90/35* (2016.02); *A61B 1/00071* (2013.01); *A61B 3/09* (2013.01);
(Continued)

(58) Field of Classification Search
CPC ............ A61B 10/0233; A61B 10/0275; A61B 17/3403; A61B 2017/00057;
(Continued)

(56) References Cited

U.S. PATENT DOCUMENTS 5,785,663 A * 7/1998 Sarvazyan ........... A61B 1/0052
                                                    600/561
5,987,346 A * 11/1999 Benaron ............... A61B 5/0059
                                                    600/407
(Continued)

FOREIGN PATENT DOCUMENTS

JP         7-54855 Y2    12/1995
JP       2008-246097 A   10/2008
(Continued)

OTHER PUBLICATIONS

International Search Report (Form PCT/ISA/210) issued in International Application No. PCT/JP2016/054770 dated Apr. 26, 2016, together with an English translation.
(Continued)

*Primary Examiner* — Eric F Winakur
*Assistant Examiner* — Chu Chuan Liu
(74) *Attorney, Agent, or Firm* — Birch, Stewart, Kolasch & Birch, LLP

(57) ABSTRACT

The length of an optical fiber from a portion aligned with the rear end of an insertion needle to a fixing portion is a length obtained by adding a predetermined extra length to a linear distance between the rear end of the insertion needle in a case where the insertion needle is located at a protruding position (insertion position) and an optical fiber fixing position of a grip portion. There is provided a fiber feeding adjustment mechanism that suspends the optical fiber with a first suspension portion and a second suspension portion so as to make a detour in a state in which there is no slack, and changes the detour length continuously according to the movement of the insertion needle in a case where the insertion needle moves between the retracted position and the protruding position, thereby maintaining a state in which the optical fiber is suspended without slack.

23 Claims, 12 Drawing Sheets

(51) Int. Cl.
*A61B 3/09* (2006.01)
*A61B 3/10* (2006.01)
*A61B 5/00* (2006.01)
*A61B 10/02* (2006.01)
*A61B 90/00* (2016.01)
*A61B 8/08* (2006.01)
*A61B 8/14* (2006.01)
*A61B 90/30* (2016.01)

(52) U.S. Cl.
CPC ............. *A61B 3/10* (2013.01); *A61B 5/0097* (2013.01); *A61B 8/0841* (2013.01); *A61B 8/14* (2013.01); *A61B 8/483* (2013.01); *A61B 8/5246* (2013.01); *A61B 8/5253* (2013.01); *A61B 10/0275* (2013.01); *A61B 90/37* (2016.02); *A61B 5/0095* (2013.01); *A61B 2090/306* (2016.02); *A61B 2090/309* (2016.02); *A61B 2090/378* (2016.02)

(58) Field of Classification Search
CPC .......... A61B 2017/3413; A61B 5/0035; A61B 5/0095; A61B 5/06; A61B 5/145; A61B 5/6848; A61B 5/6851; A61B 8/12; A61B 8/4416; G01N 2291/02475; G01N 29/22; G01N 29/2418
See application file for complete search history.

(56) References Cited

U.S. PATENT DOCUMENTS

| | | | | |
|---|---|---|---|---|
| 6,152,918 | A * | 11/2000 | Padilla | A61B 17/3403 606/15 |
| 6,564,087 | B1 * | 5/2003 | Pitris | A61B 1/00172 600/478 |
| 7,544,162 | B2 * | 6/2009 | Ohkubo | A61B 5/0066 385/117 |
| 2011/0021926 | A1 * | 1/2011 | Spencer | A61B 5/0062 600/478 |
| 2011/0319759 | A1 * | 12/2011 | Liu | A61B 10/0241 600/439 |
| 2015/0297092 | A1 | 10/2015 | Irisawa | |

FOREIGN PATENT DOCUMENTS

| | | |
|---|---|---|
| JP | 2011-67565 A | 4/2011 |
| WO | WO 2014/068468 A1 | 5/2014 |
| WO | WO 2014/109148 A1 | 7/2014 |

OTHER PUBLICATIONS

Written Opinion of the International Searching Authority (Form PCT/ISA/237) issued in PCT/JP2016/054770 dated Apr. 26, 2016, together with an English translation.

* cited by examiner

INSERTION DEVICE AND PHOTOACOUSTIC MEASUREMENT APPARATUS

CROSS-REFERENCE TO RELATED APPLICATIONS

This application is a Continuation of PCT International Application No. PCT/JP2016/054770 filed on Feb. 19, 2016, which claims priority under 35 U.S.C § 119(a) to Japanese Patent Application No. 2015-071945 filed on Mar. 31, 2015. Each of the above application(s) is hereby expressly incorporated by reference, in its entirety, into the present application.

BACKGROUND OF THE INVENTION

1. Field of the Invention

The present invention relates to a photoacoustic measurement apparatus that emits light toward a subject and receives the light to detect photoacoustic waves generated within the subject.

In addition, the present invention relates to an insertion device used in the photoacoustic measurement apparatus.

2. Description of the Related Art

In recent years, a non-invasive measurement method using a photoacoustic effect has been drawing attention. In the measurement method, a photoacoustic wave, which is an elastic wave generated as a result of emission of pulsed light having an appropriate wavelength (for example, a wavelength band of visible light, near-infrared light, or intermediate infrared light) to a subject and absorption of the energy of the pulsed light by an absorbing substance in the subject, is detected to quantitatively measure the concentration of the absorbing substance. The absorbing substance in the subject is, for example, glucose or hemoglobin contained in blood. In addition, a technique of detecting such a photoacoustic wave and generating a photoacoustic image based on the detection signal is called photo acoustic imaging (PAI) or photo acoustic tomography (PAT).

Conventionally, surgery, sample collection, and treatment such as chemical injection have been performed by inserting various insertion needles into a subject that is a living body. For example, JP2011-67565A and JP2008-246097A disclose examples of such an insertion needle. JP2011-67565A and JP2008-246097A also disclose an insertion device configured such that an insertion needle is injected to the distal end side by a biasing force, which is generated by a compression spring or the like, in order to insert the insertion needle into a subject.

In the case of performing various treatments using the above-described insertion needle, it is desirable to be able to check the distal end position of the insertion needle for the safety of the subject. WO2014/109148A discloses a technique that enables checking the distal end position of an insertion needle by applying the photo acoustic imaging. In this technique, a light guide member, such as an optical fiber, is disposed in the insertion needle so as to reach the vicinity of the distal end of the insertion needle, and a light absorber that covers the distal end of the light guide member is disposed, so that light propagated through the light guide member is incident on the light absorber from the distal end of the light guide member. Therefore, in the case of performing various treatments using the insertion needle, the distal end of the light guide member, that is, the distal end of the insertion needle can be checked by making the light incident on the light absorber from the distal end of the light guide member to generate photoacoustic waves from the light absorber, detecting the photoacoustic waves, and displaying a photoacoustic image of the light absorber.

On the other hand, JP1995-54855Y (JP-H07-54855Y) has proposed that, in order to acquire a photoacoustic image of a sample in a sample collection portion of an insertion needle (needle-shaped applicator), an optical fiber is inserted into the insertion needle between the rear end of the insertion needle and the sample collection portion, and light is emitted to the sample from the distal end of the optical fiber exposed in the sample collection portion.

SUMMARY OF THE INVENTION

In a case where the technique for making the light guide member reach the vicinity of the distal end of the insertion needle, which is disclosed in WO2014/109148A, is applied to the insertion device disclosed in JP2011-67565A or JP2008-246097A, that is, the insertion device configured such that the insertion needle is inserted to the distal end side by the biasing force generated by the compression spring or the like, the light guide member is also pulled vigorously with the injection of the insertion needle. Therefore, if the light guide member is an optical fiber, the optical fiber may be broken or damaged.

The present invention has been made in view of the above circumstances, and it is an object of the present invention to prevent an optical fiber from being broken or damaged due to injection of an insertion needle in an insertion device configured such that an insertion needle, to which an optical fiber is connected, is injected by a spring or the like.

In addition, it is an object of the present invention to provide a photoacoustic measurement apparatus including such an insertion device.

An insertion device according to an aspect of the present invention comprises: an insertion needle that is inserted into a subject from a distal end; a grip portion that holds the insertion needle so as to be movable in an axis direction of the insertion needle; a needle injection unit for injecting the insertion needle from a retracted position to a protruding position away from the retracted position toward a distal end side of the insertion needle by a predetermined injection distance; and an optical fiber that is disposed in the insertion needle to guide light from a rear end of the insertion needle. The optical fiber is fixed to the grip portion at a fixing portion that is separated from the rear end of the insertion needle to the other end side of the optical fiber. A fiber feeding adjustment mechanism is provided that suspends the optical fiber between the rear end of the insertion needle and the fixing portion in the grip portion so as to make a detour in a state in which there is no slack and changes a detour length continuously according to movement of the insertion needle in a case where the insertion needle moves between the retracted position and the protruding position, thereby maintaining a state in which the optical fiber is suspended without slack.

The "rear end" of the insertion needle means an end portion on a side opposite to the distal end.

The above-described "rearward" means a direction on a side opposite to the distal end of the insertion needle when viewed from the rear end of the insertion needle.

In addition, the above-described "detour length" refers to the length of a portion by which the optical fiber is longer than the linear distance between the rear end of the insertion needle and the optical fiber fixing position (this is the same position as a fixing portion in the optical fiber) in the grip portion.

The above-described "state in which there is no slack" is assumed to include a state in which the optical fiber is tense so as not to cause slack at all and a state in which the optical fiber is tense with minute slack to the extent that the suspension does not deviate.

Here, it is preferable that the fiber feeding adjustment mechanism has a plurality of suspension portions for suspending the optical fiber. In addition, it is preferable that the detour length of the optical fiber due to the plurality of suspension portions is continuously changed between the detour length, which absorbs the length of the optical fiber corresponding to the injection distance and the extra length in a case where the insertion needle is located at the retracted position, and the detour length, which absorbs the extra length in a case where the insertion needle is located at the protruding position, by moving at least one of the suspension portions in conjunction with the movement of the insertion needle.

More specifically, it is preferable that such a fiber feeding adjustment mechanism is configured to include: a first suspension portion that suspends the optical fiber extending rearward from the rear end of the insertion needle to change an extension direction of the optical fiber; a second suspension portion that suspends the optical fiber having passed through the first suspension portion to guide the optical fiber rearward; and a suspension portion linear driving unit for moving the first suspension portion in the same direction as an injection direction of the insertion needle in conjunction with an injection operation of the insertion needle.

As an example, it is preferable that the suspension portion linear driving unit is configured to include the needle injection unit and the optical fiber for transmitting a moving force of the insertion needle injected by the needle injection unit to the first suspension portion.

In a case where the suspension portion linear driving unit is configured as described above, it is preferable to further comprise a suspension portion biasing unit for biasing the first suspension portion in a direction opposite to the injection direction of the insertion needle.

In a case where the suspension portion linear driving unit is configured as described above, it is preferable to further comprise a contact portion that is in contact with the moving first suspension portion to define a maximum movement distance of the first suspension portion.

In addition, the suspension portion linear driving unit may be configured to include the needle injection unit and a link mechanism for transmitting a moving force of the insertion needle injected by the needle injection unit to the first suspension portion.

In addition, the suspension portion linear driving unit may be configured to include the needle injection unit and a gear mechanism for transmitting a moving force of the insertion needle injected by the needle injection unit to the first suspension portion.

In the insertion device according to an aspect of the present invention, it is preferable that the fiber feeding adjustment mechanism is configured to include: a first suspension portion that suspends the optical fiber extending rearward from the rear end of the insertion needle to change an extension direction of the optical fiber; a second suspension portion that suspends the optical fiber having passed through the first suspension portion to guide the optical fiber rearward; and a suspension portion linear driving unit for moving the second suspension portion in a direction opposite to an injection direction of the insertion needle in conjunction with an injection operation of the insertion needle.

In a case where the fiber feeding adjustment mechanism is configured as described above, it is preferable that the suspension portion linear driving unit is configured to include the needle injection unit and a link mechanism for transmitting a moving force of the insertion needle injected by the needle injection unit to the second suspension portion.

In addition, the suspension portion linear driving unit may be configured to include the needle injection unit and a gear mechanism for transmitting a moving force of the insertion needle injected by the needle injection unit to the second suspension portion.

On the other hand, in the insertion device according to an aspect of the present invention, it is preferable that the first and second suspension portions are disposed so as to suspend the optical fiber in an S shape.

In the insertion device according to an aspect of the present invention, the fiber feeding adjustment mechanism may be configured to include: a first suspension portion that suspends the optical fiber extending rearward from the rear end of the insertion needle to change an extension direction of the optical fiber; a second suspension portion that suspends the optical fiber having passed through the first suspension portion to guide the optical fiber rearward; a rotating pedestal that is rotatable around a shaft perpendicular to a surface, on which the optical fiber suspended on the first suspension portion and the second suspension portion extends, while holding the first and second suspension portions; and a suspension portion rotation driving unit for rotating the rotating pedestal in a direction, in which the first suspension portion approaches the insertion needle, in conjunction with an injection operation of the insertion needle.

The above-described "surface on which the optical fiber extends" means one surface including the centerline of the optical fiber.

Here, it is preferable that the suspension portion rotation driving unit is configured to include the needle injection unit and a link mechanism for transmitting a moving force of the insertion needle injected by the needle injection unit to the rotating pedestal.

Alternatively, the suspension portion rotation driving unit may be configured to include the needle injection unit and a gear mechanism for transmitting a moving force of the insertion needle injected by the needle injection unit to the rotating pedestal.

In the insertion device according to an aspect of the present invention, it is preferable that at least one of the first suspension portion or the second suspension portion is configured to suspend the optical fiber on a pulley.

Alternatively, in the insertion device according to an aspect of the present invention, it is preferable that at least one of the first suspension portion or the second suspension portion is configured to suspend the optical fiber on a member having a convex curved surface for sliding the optical fiber.

In the insertion device according to an aspect of the present invention, it is preferable to further comprise a guide unit for changing the extension direction of the optical fiber, which is located between the rear end of the insertion needle and the first suspension portion.

In the insertion device according to an aspect of the present invention, it is preferable that the rear end of the insertion needle is fixed to a base and the insertion needle is injected through the base.

In the insertion device according to an aspect of the present invention, it is preferable that the needle injection unit is configured to inject the insertion needle with a spring force.

In the insertion device according to an aspect of the present invention, it is preferable that the insertion needle is a biopsy needle having a recessed sample collection portion cut inward from an outer peripheral surface.

In the insertion device according to an aspect of the present invention, it is preferable that the insertion needle is an inner needle in an insertion needle unit having a hollow tubular outer needle and an inner needle that is housed in the outer needle and is movable in a tube axis direction of the outer needle.

In a case where the above-described insertion needle unit is applied, an outer needle injection unit for injecting the outer needle in the same direction as an injection direction of the inner needle, which is the insertion needle, may be further comprised.

On the other hand, a photoacoustic measurement apparatus according to an aspect of the present invention comprises the insertion device according to the present invention described above.

In the insertion device according to an aspect of the present invention, the optical fiber between the rear end of the insertion needle and the fixing portion in the grip portion is suspended so as to make a detour in a state in which there is no slack, and the detour length is continuously changed according to the movement of the insertion needle in a case where the insertion needle moves between the retracted position and the protruding position, so that a state in which the optical fiber is suspended without slack is maintained. Therefore, it is possible to prevent the optical fiber from being broken or damaged due to the injection of the insertion needle.

DESCRIPTION OF THE PREFERRED EMBODIMENTS

Hereinafter, embodiments of the present invention will be described in detail with reference to the diagrams.

Figure 1:
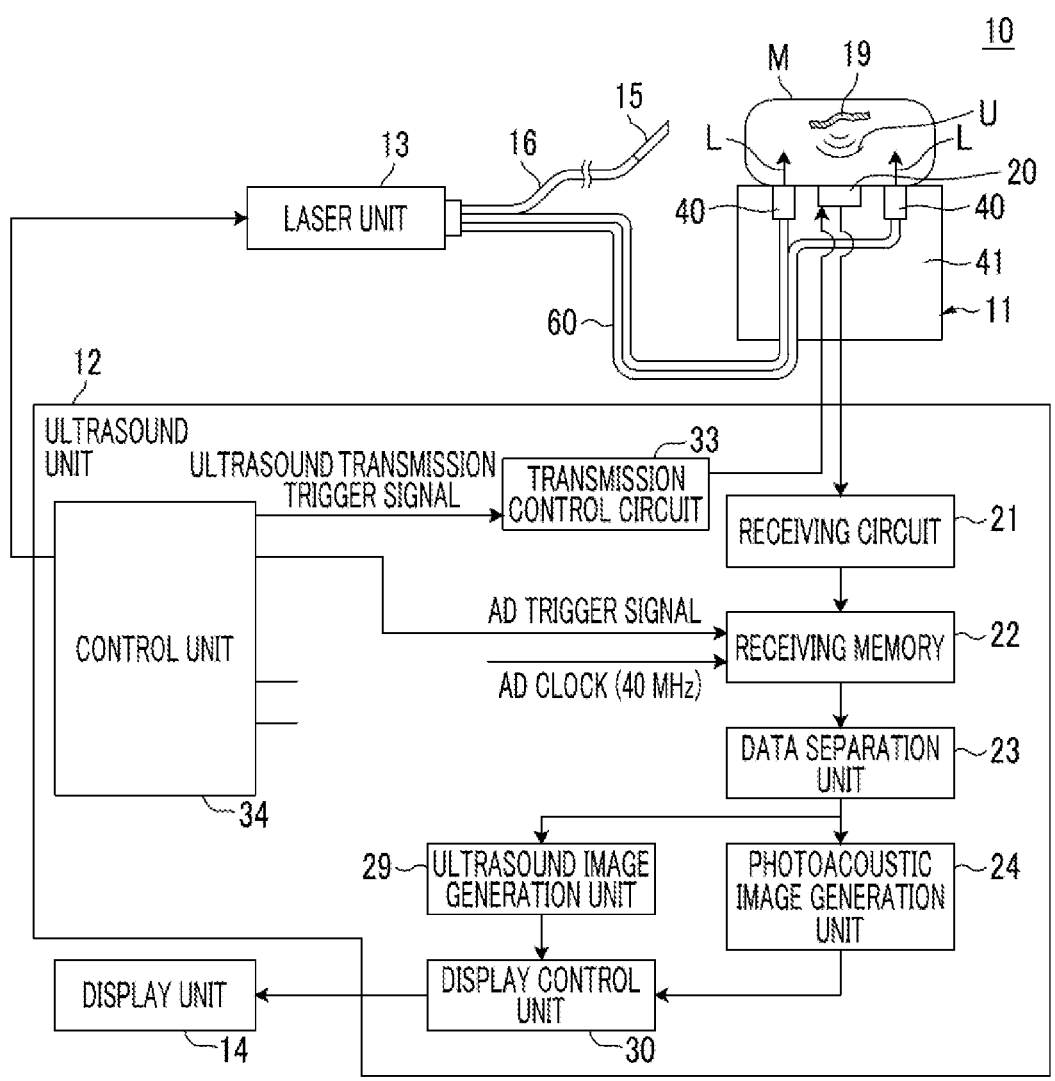
FIG. 1 is a schematic diagram showing the overall configuration of a photoacoustic measurement apparatus according to an embodiment of the present invention.

First, a photoacoustic measurement apparatus that is an embodiment of the present invention will be described. FIG. 1 is a schematic diagram showing the overall configuration of a photoacoustic measurement apparatus 10 of the present embodiment. In FIG. 1, the shapes of a probe 11 and an insertion device 15, which will be described later, are schematically shown.

As an example, the photoacoustic measurement apparatus 10 of the present embodiment has a function of generating a photoacoustic image based on a photoacoustic signal, and includes the probe (ultrasound probe) 11, an ultrasound unit 12, a laser unit 13, a display unit 14, the insertion device 15, and the like as schematically shown in FIG. 1. Hereinafter, these components will be described in a sequential manner.

The probe 11 has, for example, a function of emitting measurement light and an ultrasound wave toward a subject M, which is a living body, and a function of detecting an acoustic wave U propagating through the subject M. That is, the probe 11 can emit (transmit) ultrasound waves to the subject M and detect (receive) reflected ultrasound waves (reflected acoustic waves) that return due to reflection from the subject M. The probe 11 can also detect photoacoustic waves generated in the subject M. In this specification, the term "acoustic wave" is a term including ultrasound waves and photoacoustic waves. Here, the "ultrasound wave" means an elastic wave transmitted by a probe and its reflected wave, and the "photoacoustic wave" means an elastic wave emitted by absorbing measurement light by the absorber 19. As the absorber 19 in the subject M, for example, blood vessels, a metal member, and the like can be mentioned.

The probe 11 includes a transducer array 20 that is an acoustic wave detection element, a total of two light emitting units 40 disposed on both sides of the transducer array 20 with the transducer array 20 interposed therebetween, and a housing 41 in which the transducer array 20 and the two light emitting units 40 are housed.

In the present embodiment, the transducer array 20 also functions as an ultrasound wave transmission element. The transducer array 20 is connected to an ultrasound wave transmission circuit in a transmission control circuit 33 and an acoustic wave receiving circuit in a receiving circuit 21 through a wiring 20a. An optical fiber 42 as a connection unit for guiding laser light L, which is measurement light emitted from the laser unit 13 to be described later, to the light emitting unit 40 is connected to the probe 11.

The transducer array 20 is configured to include a plurality of ultrasound transducers arranged in a one-dimensional or two-dimensional manner, for example. The ultrasound transducer is, for example, a piezoelectric element formed of a polymer film, such as piezoelectric ceramics or polyvinylidene fluoride (PVDF). The ultrasound transducer has a function of converting the received acoustic wave U into an electrical signal. The electrical signal output from the transducer array 20 is input to the receiving circuit 21 to be described later. Generally, the probe 11 corresponding to sector scanning, the probe 11 corresponding to linear scanning, the probe 11 corresponding to convex scanning, and the like are prepared. Among these, an appropriate one selected according to an imaging part is used. The transducer array 20 may include an acoustic lens.

The ultrasound transducer also has a function of transmitting ultrasound waves. That is, in a case where an alternating voltage is applied to the ultrasound transducer, the ultrasound transducer generates ultrasound waves having a frequency corresponding to the frequency of the alternating voltage. Transmission and reception of ultrasound waves may be separated from each other. That is, for example, ultrasound waves may be transmitted from a position different from the probe 11, and reflected ultrasound waves of the transmitted ultrasound waves may be received by the probe 11.

The light emitting unit 40 is a unit that emits the laser light L guided by the optical fiber 42 to the subject M. In the present embodiment, the two light emitting units 40 are disposed on both sides of the transducer array 20, for example, in the elevation direction (in a case where a plurality of ultrasound transducers are arranged in a one-dimensional manner, a direction that is perpendicular to the arrangement direction and is parallel to the detection surface) with the transducer array 20 interposed therebetween.

The laser unit 13 has, for example, a flash lamp excitation Q-switch solid state laser, such as a Q-switch alexandrite laser, and emits the laser light L as measurement light that is emitted to the subject M. The laser unit 13 is configured to receive a trigger signal from a control unit 34 of the ultrasound unit 12 and output the laser light L, for example. It is preferable that the laser unit 13 outputs the pulsed laser light L having a pulse width of 1 to 100 nsec (nanoseconds).

The wavelength of the laser light L is appropriately selected according to the light absorption characteristics of the absorber 19 in the subject M that is a measurement target. For example, in a case where the measurement target is hemoglobin in the living body, that is, in the case of imaging blood vessels, it is generally preferable that the wavelength is a wavelength belonging to the near-infrared wavelength range. The near-infrared wavelength range means a wavelength range of approximately 700 nm to 850 nm. However, it is natural that the wavelength of the laser light L is not limited thereto. In addition, the laser light L may have a single wavelength, or may include a plurality of wavelengths of, for example, 750 nm and 800 nm. In a case where the laser light L includes a plurality of wavelengths, light beams having these wavelengths may be simultaneously emitted to the subject M, or may be emitted while being switched alternately.

In addition to the alexandrite laser described above, the laser unit 13 can be formed by using a YAG-second harmonic generation (SHG)-optical parametric oscillation (OPO) laser, a Ti-Sapphire (titanium sapphire) laser, or the like capable of outputting laser light in the near-infrared wavelength range similarly.

The optical fiber 42 guides the laser light L emitted from the laser unit 13 to the two light emitting units 40. The optical fiber 42 is not particularly limited, and known fibers, such as a quartz fiber, can be used. For example, one thick optical fiber may be used, or a bundle fiber in which a plurality of optical fibers are bundled may be used. As an example, in a case where a bundle fiber is used, the bundle fiber is arranged so that the laser light L is incident from the light incidence end surface of a group of fiber portions, and the light emitting units 40 are coupled to the light emitting end surfaces of the two branched fiber portions of the bundle fiber.

The ultrasound unit 12 has the receiving circuit 21, a receiving memory 22, a data separation unit 23, a photoacoustic image generation unit 24, an ultrasound image generation unit 29, a display control unit 30, the transmission control circuit 33, and the control unit 34.

The control unit 34 controls each unit of the photoacoustic measurement apparatus 10, and includes a trigger control circuit (not shown) in the present embodiment. The trigger control circuit transmits an optical trigger signal to the laser unit 13, for example, in the case of acquiring a photoacoustic image. As a result, the flash lamp of the excitation source is turned on in the Q-switch solid state laser of the laser unit 13, and excitation of the laser rod is started. While the excitation state of the laser rod is maintained, the laser unit 13 is ready to output the laser light L.

Thereafter, the control unit 34 transmits a Q-switch trigger signal to the laser unit 13 from the trigger control circuit. That is, the control unit 34 controls the output timing of the laser light L from the laser unit 13 using the Q-switch trigger signal. The control unit 34 transmits a sampling trigger signal to the receiving circuit 21 in synchronization with the transmission of the Q-switch trigger signal. This sampling trigger signal specifies the sampling start timing of the photoacoustic signal in an analog to digital converter (AD converter) of the receiving circuit 21. Thus, it is possible to sample a photoacoustic signal in synchronization with the output of the laser light L by using the sampling trigger signal.

In the case of acquiring an ultrasound image, the control unit 34 transmits an ultrasound wave transmission trigger signal for giving an instruction to transmit ultrasound waves to the transmission control circuit 33. In a case where the ultrasound wave transmission trigger signal is received, the transmission control circuit 33 makes the probe 11 transmit ultrasound waves. The control unit 34 transmits a sampling trigger signal to the receiving circuit 21 according to the timing of ultrasound wave transmission, thereby starting the sampling of a reflected ultrasound signal.

The receiving circuit 21 receives a detection signal output from the probe 11, and stores the received detection signal in the receiving memory 22. Typically, the receiving circuit 21 is configured to include a low noise amplifier, a variable gain amplifier, a low pass filter, and an AD converter. The detection signal of the probe 11 is amplified by the low noise amplifier, and then gain adjustment according to the depth is performed by the variable gain amplifier and a high-frequency component is cut by the low pass filter. Then, conversion into a digital signal is performed by the AD converter, and the digital signal is stored in the receiving memory 22. The receiving circuit 21 is formed by one integrated circuit (IC), for example.

In the present embodiment, the probe 11 outputs a detection signal of photoacoustic waves and a detection signal of reflected ultrasound waves. Therefore, digitized detection signals (sampling data) of photoacoustic waves and reflected ultrasound waves are stored in the receiving memory 22. The data separation unit 23 reads the sampling data (photoacoustic data) of the photoacoustic wave detection signal from the receiving memory 22, and transmits the sampling data to the photoacoustic image generation unit 24. The data separation unit 23 reads the sampling data (reflected ultrasound data) of the reflected ultrasound detection signal from the receiving memory 22, and transmits the sampling data to the ultrasound image generation unit 29.

The photoacoustic image generation unit 24 reconstructs data of one line by adding the pieces of photoacoustic data stored in the receiving memory 22 to each other with a delay time corresponding to the position of the transducer array 20 of the probe 11, and generates data of a tomographic image (photoacoustic image) based on the photoacoustic data of each line. The photoacoustic image generation unit 24 may perform reconstruction using a circular back projection (CBP) instead of the delay addition method. Alternatively, the photoacoustic image generation unit 24 may perform reconstruction using a Hough transform method or a Fourier transform method. The photoacoustic image generation unit 24 outputs the data of the photoacoustic image generated as described above to the display control unit 30.

The ultrasound image generation unit 29 generates data of a tomographic image (ultrasound image) by performing basically the same processing as for the photoacoustic data on the reflected ultrasound data stored in the receiving memory 22. The ultrasound image generation unit 29 outputs the data of the ultrasound image generated as described above to the display control unit 30.

The display control unit 30 displays a photoacoustic image on the display unit 14 based on the data of the photoacoustic image, and displays an ultrasound image on the display unit 14 based on the data of the ultrasound image. These two images are separately displayed on the display unit 14, or are combined to be displayed on the display unit 14 as a composite image. In the latter case, the display control unit 30 performs image combination by superimposing the photoacoustic image and the ultrasound image, for example. In this manner, if the ultrasound image is generated and displayed in addition to the photoacoustic image, a portion that can not be imaged in the photoacoustic image can be observed in the ultrasound image. Therefore, by using a tissue, such as a bone or a nerve drawn in the ultrasound image, as a landmark, it is possible to understand at which position, for example, a blood vessel or an insertion needle shown in the photoacoustic image is present more easily than in a case where a photoacoustic image is independently observed.

By alternately acquiring the ultrasound image and the photoacoustic image, it is possible to reduce the shift of image position due to the acquisition timing of the photoacoustic image and the ultrasound image.

In addition, by scanning the subject M in the above elevation direction with the probe 11 so that a plurality of photoacoustic images or ultrasound images can be obtained, it is possible to construct a three-dimensional image. The scanning may be performed by manually moving the probe 11 by the operator or may be performed using an automatic scanning mechanism.

In the photoacoustic measurement apparatus 10 of the present embodiment, the insertion device 15 including a biopsy needle that is an insertion needle is provided. The insertion device 15 inserts the biopsy needle into the subject M in order to collect a living tissue (biological sample) inside the subject M. The insertion device 15 includes an optical fiber 16 as a light guide member, and the optical fiber 16 is connected to the laser unit 13.

Next, an embodiment of the insertion device of the present invention will be described.

<First Embodiment of an Insertion Device>

Figure 2:
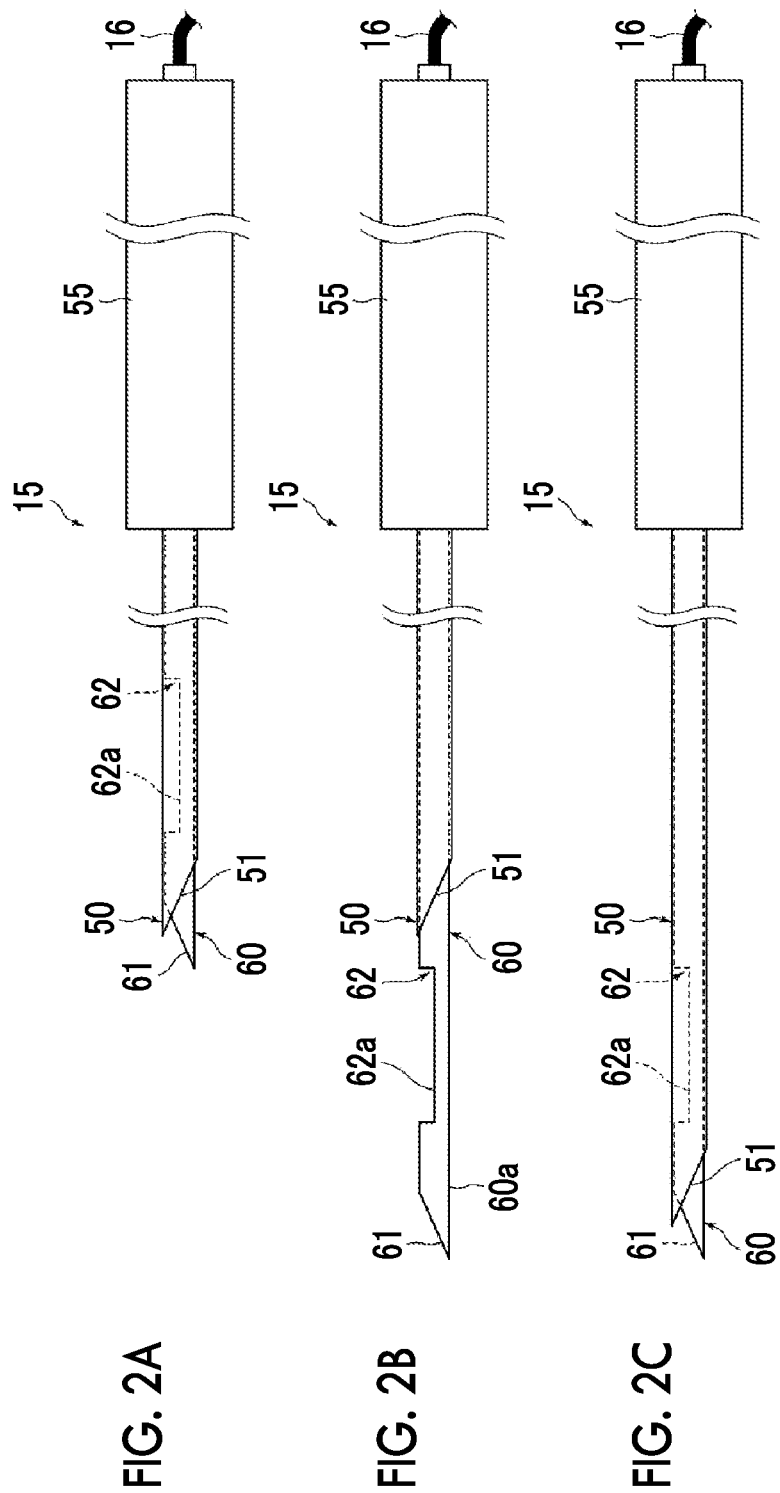
FIGS. 2A to 2C are schematic diagrams showing three states in a case where an insertion device according to a first embodiment of the present invention is used.

First, the insertion device 15 according to a first embodiment of the present invention will be described. First, with reference to 2A to 2C, the basic structure of the insertion device 15 will be described. The insertion device 15 has a hollow tubular outer needle 50, which is held by a grip portion (handle) 55 gripped by an operator, and an inner needle 60, which is disposed in the hollow portion of the outer needle 50 so as to be movable in the tube axis direction relative to the outer needle 50. The inner needle 60 has a rod shape, and the axis direction matches the tube axis direction of the outer needle 50. That is, the inner needle 60 relatively moves the inside of the outer needle 50 in its axis direction. The optical fiber 16 described above is connected to the inner needle 60. In FIGS. 2A to 2C, the arrangement state of the grip portion 55 and the optical fiber 16 in the inner needle 60 is not shown.

The outer needle 50 is formed of, for example, metal, and its distal end 51 is obliquely cut. On the other hand, the inner needle 60 is formed of, for example, a metal member having an approximately cylindrical shape, and its distal end 61 is obliquely cut. The outer needle 50 and the inner needle 60 are combined, for example, in a state in which the directions of cuts of the respective distal ends are different from each other by 180°, thereby forming an insertion needle unit. The distal end 51 of the outer needle 50 and the distal end 61 of the inner needle 60 are end portions on a side of inserted into the subject M, which is an opposite side to a side where the optical fiber 16 is connected. In the inner needle 60, a sample collection portion 62 is provided at a position spaced a predetermined distance from the distal end toward the rear end side. The sample collection portion 62 is a recessed portion cut inward from a circumferential surface 60a of the inner needle 60.

In the grip portion 55, rear end portions of the outer needle 50 and the inner needle 60, that is, end portions of the outer needle 50 and the inner needle 60 on a side where a base of a needle to be described later is mounted are housed. In the grip portion 55, a needle injection unit for injecting the outer needle 50 and the inner needle 60 to the front end side is provided for each needle. The needle injection unit and the base will be described in detail later.

Hereinafter, a biological sample collection operation of the insertion device 15 will be described. First, as shown in FIG. 2A, the outer needle 50 and the inner needle 60 are inserted into the subject M (refer to FIG. 1) that is a living body, for example, in a state in which the distal end 51 of the outer needle 50 and the distal end 61 of the inner needle 60 are substantially aligned. In this case, the outer needle 50 and the inner needle 60 are inserted so that the distal ends 51 and 61 are located slightly in front of a sampling part of the subject M. The injection operation described above is performed by an operator who grips the grip portion 55 of the insertion device 15.

Then, as shown in FIG. 2B, the inner needle 60 is injected (moved forward) to the distal end side by the above-described needle injection unit, so that the sample collection portion 62 is moved into the sampling part. Then, as shown in FIG. 2C, the outer needle 50 is moved forward to a position where the distal end 51 exceeds the sample collection portion 62. The forward movement of the outer needle 50 is also performed by the above-described needle injection unit. Therefore, a biological sample is cut off by the distal end 51 of the outer needle, and the cut sample is held in the sample collection portion 62 in the outer needle 50. Then, the outer needle 50 and the inner needle 60 are removed from the subject M, and the outer needle 50 is retracted to the grip portion 55 side. As a result, the sample held by the sample collection portion 62 is taken out.

Figure 3:
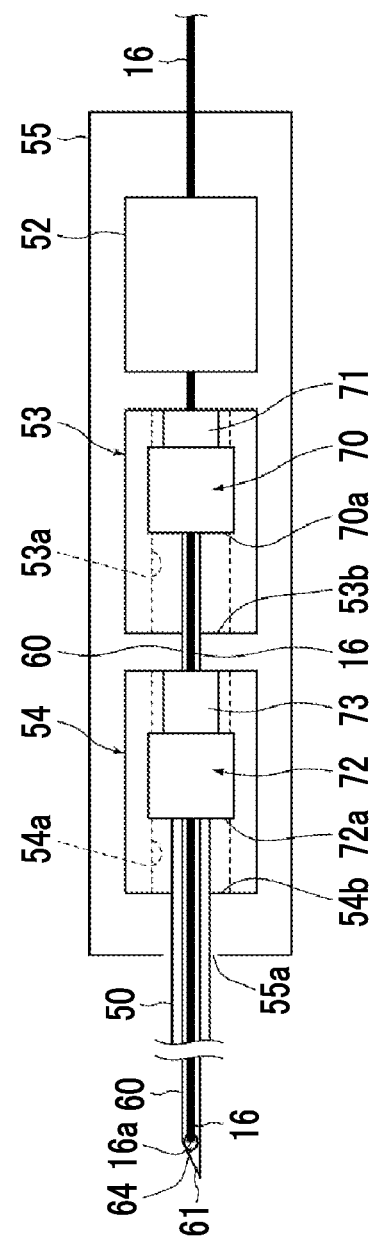
FIG. 3 is a schematic diagram showing the configuration of the insertion device according to the first embodiment of the present invention as blocks.
Figure 4:
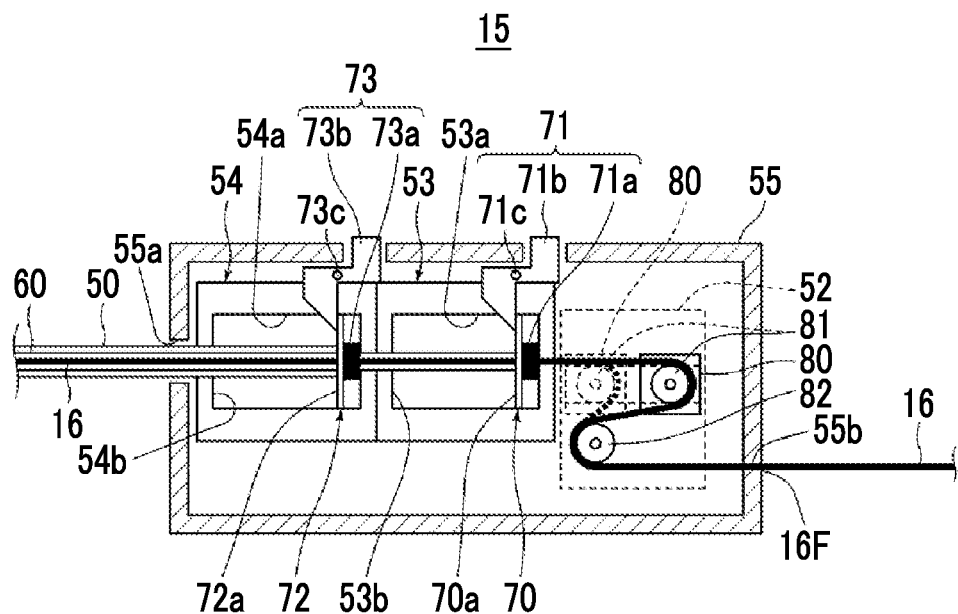
FIG. 4 is a partially broken side view showing the insertion device according to the first embodiment.
Figure 5:
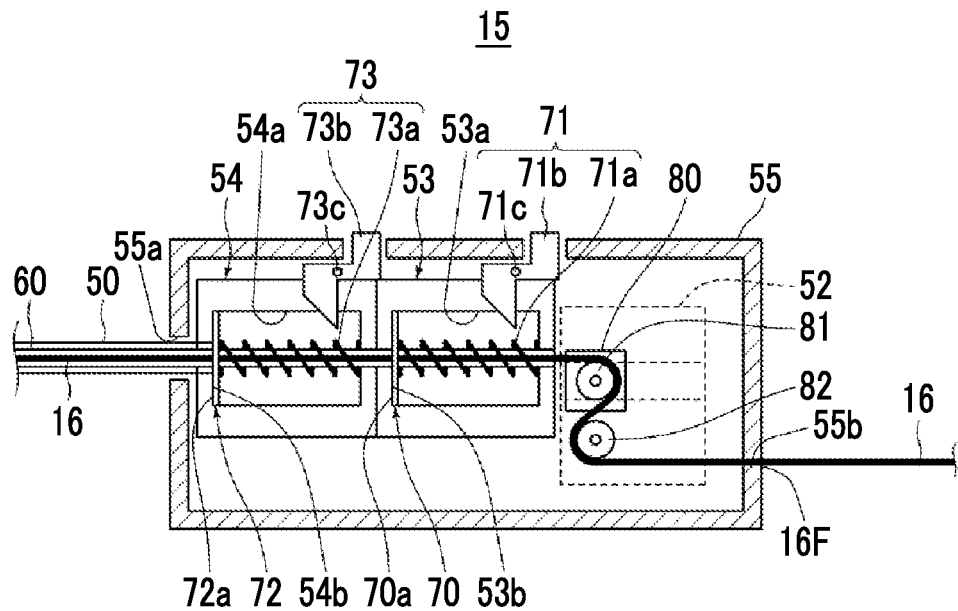
FIG. 5 is a partially broken side sectional view showing that the insertion device shown in FIG. 4 is in another state.

Next, a more detailed configuration of the insertion device 15 of the present embodiment will be described with reference to FIGS. 3 to 5. FIG. 3 schematically shows the components of the insertion device 15 as blocks, and FIGS. 4 and 5 show the insertion device 15 in a direction at the time of use in a case where the insertion device 15 is cut along a vertical plane including the central axis of the outer needle 50 and the inner needle 60. The "direction at the time of use" is a direction in which a bottom surface 62a of the sample collection portion 62 shown in FIGS. 2A to 2C faces upward in the vertical direction.

As shown in FIG. 3, in addition to the outer needle 50, the inner needle 60, and the grip portion 55 that have described above, the insertion device 15 has a fiber feeding adjustment mechanism 52, an inner needle holding portion 53, and an outer needle holding portion 54 that are disposed in the grip portion 55.

In the inner needle holding portion 53, an inner needle base 70 and an inner needle injection unit 71 to which the rear end portion of the inner needle 60 is fixed are attached. The inner needle holding portion 53 has an inner needle guide portion 53a that defines a space extending in the horizontal direction in the diagram and a front wall 53b that is the front end of the space. The inner needle base 70 is disposed in the space, and is held so as to be movable in the horizontal direction in the diagram, that is, in the axis direction of the inner needle 60 along the inner needle guide portion 53a. The inner needle injection unit 71 causes the inner needle base 70, which is movable as described above, to be injected (moved forward) in the left direction in the diagram, that is, to the distal end 61 side of the inner needle 60. Before this injection, the inner needle base 70 is located at a position shown in FIG. 3. In this state, the inner needle 60 is located at a position (retracted position) shown in FIG. 2A. In a case where the above injection is made, a front end 70a of the inner needle base 70 moves forward to a position where the front end 70a is in contact with the front wall 53b of the inner needle holding portion 53. In this case, the inner needle 60 reaches a position (protruding position) shown in FIGS. 2B and 2C. That is, the front wall 53b that is a contact portion in the present invention accurately defines the maximum movement distance of the inner needle 60.

On the other hand, in the outer needle holding portion 54, an outer needle base 72 and an outer needle injection unit 73 to which the rear end portion of the outer needle 50 is fixed are attached. The outer needle holding portion 54 has an outer needle guide portion 54a that defines a space extending in the horizontal direction in the diagram and a front wall 54b that is the front end of the space. The outer needle base 72 is disposed in the space, and is held so as to be movable in the horizontal direction in the diagram, that is, in the axis direction of the outer needle 50 along the outer needle guide portion 54a. The outer needle injection unit 73 causes the outer needle base 72, which is movable as described above, to be injected in the left direction in the diagram, that is, to the distal end 51 side of the outer needle 50 (refer to FIGS. 2A to 2C). Before this injection, the outer needle base 72 is located at a position shown in FIG. 3. In this state, the outer needle 50 is located at a position (retracted position) shown in FIGS. 2A and 2B. In a case where the above injection is made, a front end 72a of the outer needle base 72 moves forward to a position where the front end 72a is in contact with the front wall 54b of the outer needle holding portion 54. In this case, the outer needle 50 reaches a position (protruding position) shown in FIG. 2C.

The outer needle 50 can move back and forth through an opening 55a provided in the front wall portion of the grip portion 55. As described above, the inner needle 60 is housed in the outer needle 50 so as to be movable in the tube axis direction of the outer needle 50. As a result, the inner needle 60 can move back and forth in a manner of passing through the opening 55a.

An operation of returning the outer needle 50 and the inner needle 60, which have been injected to the protruding position as described above, to the original retracted position will be described in detail later.

In the inner needle 60, the optical fiber 16 shown by a thick line in the diagram is disposed such that the distal end 16a (left end in FIG. 3 and one end of the optical fiber in the present invention) is located in the vicinity of the distal end 61 of the inner needle 60. The optical fiber 16 is disposed, for example, by drilling an inner hole that extends over the entire length of the inner needle 60 and inserting the optical fiber 16 through the inner hole. Light from the rear end (right end in FIG. 3 and the other end of the optical fiber in the present invention) side is incident on the optical fiber 16. The optical fiber 16 guides the light to be emitted from the distal end 16a. In the vicinity of the distal end 61 of the inner needle 60, the light absorber 64 is disposed so as to cover the distal end 16a of the optical fiber 16. The light absorber 64 is formed of a material that absorbs light emitted from the distal end 16a of the optical fiber 16, for example, a synthetic resin, such as an epoxy resin, a fluororesin, or a polyurethane resin mixed with a black pigment.

The phrase "distal end 16a is located in the vicinity of the distal end 61 of the inner needle 60" means that the distal end 16a of the optical fiber 16 is present at a position where photoacoustic waves emitted from the light absorber 64, which has absorbed the light emitted from the distal end 16a of the optical fiber 16, can propagate from the distal end 61 of the inner needle 60 to the outside and be detected by the probe 11 shown in FIG. 1 in a state in which the inner needle 60 is inserted into the subject M.

The light absorber 64 also acts as an adhesive, and bonds and fixes the optical fiber 16 to the inner needle 60. The optical fiber 16 may be more firmly fixed to the inner needle 60 using other adhesives or the like.

As an example, the outer diameter of a portion of the inner needle 60 where the sample collection portion 62 is not formed is about 0.9 to 1.2 mm, and the outer diameter of the optical fiber 16 is about 0.1 to 0.2 mm. In terms of easy layout between the laser unit 13 and the grip portion 55 and difficulty of breakage, it is preferable that the optical fiber 16 is thinner as long as the light guiding property is not adversely affected. On the other hand, the biopsy needle is defined by JIS T3228 "Biopsy needle for living tissue collection". Among these, the thickness of the inner needle is described to ensure rigidity in "A. 1. 2 Thickness of an inner needle having a sample collection space portion for tissue diagnosis". However, there is no particular numerical specification, and the outer diameter of the inner needle 60 is also an example.

As described above with reference to FIGS. 2A to 2C, in the case of inserting the insertion device 15 into the subject M to collect a biological sample, light emitted from the laser unit 13 shown in FIG. 1 is incident on the optical fiber 16 from the rear end side (right end side in FIG. 3). In this example, the light is the same laser light L as the light emitted from the probe 11. The light propagates through the optical fiber 16, is emitted from the distal end 16a of the optical fiber 16, and is absorbed by the light absorber 64. Photoacoustic waves are emitted from a portion of the light absorber 64 that has absorbed light, that is, a portion close to the distal end 16a of the optical fiber 16.

In the case of collecting a biological sample as described above, the laser light L is also emitted from the probe 11 shown in FIG. 1. Accordingly, the photoacoustic image of the subject M is displayed on the display unit 14 as described above. In this case, since the photoacoustic waves are emitted as described above from the portion of the light absorber 64 close to the distal end 16a of the optical fiber 16 and the photoacoustic waves are detected by the probe 11, a photoacoustic image of the portion of the light absorber 64 is also displayed on the display unit 14. In a case where the photoacoustic image of the portion of the light absorber 64 close to the distal end 16a of the optical fiber 16 is displayed in this manner, the operator can check where the distal end 16a of the optical fiber 16, that is, the distal end 61 of the inner needle 60 is located with reference to the display. Therefore, in the case of collecting a biological sample, it is possible to perform safe insertion and appropriate tissue collection.

Next, the more specific configuration of the insertion device 15 of the present embodiment will be described with reference to FIGS. 4 and 5. In these diagrams, the same elements as in FIGS. 2A to 2C or FIG. 3 described previously are denoted by the same reference numerals, and the explanation thereof will be omitted unless particularly required (the same hereinbelow).

FIG. 4 is a partially broken side view showing the insertion device 15 in a case where the outer needle 50 and the inner needle 60 are located at the above-described retracted position. On the other hand, FIG. 5 is a partially broken side view showing the insertion device 15 in a case where the outer needle 50 and the inner needle 60 are located at the above-described protruding position. In FIG. 4, a first suspension portion 81 in a case where the outer needle 50 and the inner needle 60 are located at the protruding position is also shown by a broken line.

As shown in FIGS. 4 and 5, the inner needle base 70 is, for example, a disk-shaped member. The inner needle injection unit 71 is configured to include a coil spring 71a and a trigger member 71b having a shape shown in the diagram. The trigger member 71b has a triangular piece-like lower portion and an upper portion, which slightly protrudes outward from the opening of the grip portion 55, and is held so as to freely reciprocate and rotate around a rotation shaft 71c. As shown in FIG. 4, the inner needle base 70 is prevented from moving forward by the trigger member 71b in a state where the coil spring 71a is compressed, and sets the inner needle 60 at the retracted position.

In a case where the upper portion of the trigger member 71b is pushed downward in this state, the trigger member 71b rotates clockwise in the diagram around the rotation shaft 71c, so that the inner needle base 70 is released from the trigger member 71b. Therefore, the coil spring 71a that is compressed to store the energy expands to change to the state shown in FIG. 5, thereby pushing the inner needle base 70 so that the inner needle 60 is injected (moved forward) as described above. In this manner, the inner needle 60 is set at the protruding position. Thereafter, for example, in a case where the inner needle 60 is retracted (moved to the right in the diagram) by manual operation, the inner needle base 70 pushes the inclined surface of the lower portion of the trigger member 71b to return to the state shown in FIG. 4 over the inclined surface while rotating the trigger member 71b counterclockwise in the diagram around the rotation shaft 71c. As a result, the coil spring 71a is compressed again to return to the energy-stored state.

The configuration for injecting the outer needle 50 is also basically the same as the above-described configuration. That is, the outer needle base 72 is, for example, a disk-shaped member. The outer needle injection unit 73 is configured to include a coil spring 73a and a trigger member 73b having a shape shown in the diagram. The trigger member 73b has a triangular piece-like lower portion and an upper portion, which slightly protrudes outward from the opening of the grip portion 55, and is held so as to freely reciprocate and rotate around a rotation shaft 73c. As shown in FIG. 4, the outer needle base 72 is prevented from moving forward by the trigger member 73b in a state where the coil spring 73a is compressed, and sets the outer needle 50 at the retracted position.

In a case where the upper portion of the trigger member 73b is pushed downward in this state, the trigger member 73b rotates clockwise in the diagram around the rotation shaft 73c, so that the outer needle base 72 is released from the trigger member 73b. Therefore, the coil spring 73a that stores energy by the compression expands to change to the state shown in FIG. 5, thereby pushing the outer needle base 72 so that the outer needle 50 is injected (moved forward) as described above. In this manner, the outer needle 50 is set at the protruding position. Thereafter, for example, in a case where the outer needle 50 is retracted (moved to the right in the diagram) by manual operation, the outer needle base 72 pushes the inclined surface of the lower portion of the trigger member 73b to return to the state shown in FIG. 4 over the inclined surface while rotating the trigger member 73b counterclockwise in the diagram around the rotation shaft 73c. As a result, the coil spring 73a is compressed again to return to the energy-stored state.

The operation of retracting the outer needle 50 or the inner needle 60 as described above is not limited to the manual operation, but may be performed using a spring force or the like.

Next, the fiber feeding adjustment mechanism 52 will be described. The optical fiber 16 is fixed to the grip portion 55 at a fixing portion 16F that is separated from the rear end of the inner needle 60 toward the rear end side of the optical fiber 16. In the present embodiment, the rear end of the inner needle 60 matches the rear end of the inner needle base 70. The length of the optical fiber 16 from a portion aligned with the rear end of the inner needle 60 to the fixing portion 16F is a length obtained by adding a predetermined extra length to a linear distance between the rear end of the inner needle 60 in a case where the inner needle 60 is located at the protruding position and an optical fiber fixing position 55b (this is the same position as the fixing portion 16F) of the grip portion 55.

The fiber feeding adjustment mechanism 52 suspends the optical fiber 16 between the rear end of the inner needle 60 and the optical fiber fixing position 55b so as to make a detour in a state in which there is no slack, and changes the detour length continuously according to the movement of the inner needle 60 in a case where the inner needle 60 moves between the retracted position and the protruding position, thereby maintaining a state in which there is no slack in the optical fiber 16. The above-described "state in which there is no slack" is assumed to include a state in which the optical fiber 16 is tense so as not to cause slack at all and a state in which the optical fiber 16 is tense with minute slack to the extent that the suspension does not deviate. In addition, the above-described "detour length" refers to the length of a portion by which the optical fiber is longer than the linear distance between the rear end of the inner needle 60 and the optical fiber fixing position 55b.

Hereinafter, a more detailed configuration of the fiber feeding adjustment mechanism 52 will be described. The fiber feeding adjustment mechanism 52 has the first suspension portion 81 for suspending the optical fiber 16 extending rearward from the rear end of the inner needle 60 to change the extension direction of the optical fiber 16, a second suspension portion 82 for suspending the optical fiber 16 having passed through the first suspension portion 81 to guide the optical fiber 16 rearward, and a suspension portion linear driving unit for moving the first suspension portion 81 in the same direction as the injection direction of the inner needle 60, that is, to the left in FIG. 4 in conjunction with the injection operation of the inner needle 60. In the present embodiment, each of the first suspension portion 81 and the second suspension portion 82 is configured to suspend the optical fiber 16 on a rotating pulley, and the optical fiber 16 is suspended in an approximately S shape by the suspension portions 81 and 82.

In the present embodiment, the suspension portion linear driving unit is configured to include the inner needle injection unit 71 described above, the optical fiber 16 for transmitting the moving force of the inner needle 60 injected by the inner needle injection unit 71 to the first suspension portion 81, and a pedestal 80.

The pedestal 80 is held by guide holding unit (not shown) so as to be movable in the same direction as the movement direction of the inner needle 60, that is, in the horizontal direction in FIG. 4, in the fiber feeding adjustment mechanism 52. The pedestal 80, that is, the first suspension portion 81 is biased in a direction opposite to the injection direction of the inner needle 60, that is, to the right in FIG. 4, by a suspension portion biasing unit such as a spring (not shown). The biasing force is set to be smaller than the injection force of the coil spring 71a forming the inner needle injection unit 71.

In the above configuration, in a case where the inner needle 60 is injected from the state of FIG. 4 as described above, the optical fiber 16 fixed to the inner needle 60 also moves forward together with the inner needle 60. Therefore, the first suspension portion 81 is pulled by the optical fiber 16 against the biasing force of the suspension portion biasing unit, and moves continuously from the position shown in FIG. 4 to the position shown in FIG. 5 in conjunction with the movement of the inner needle 60.

In this manner, corresponding to the forward movement of the optical fiber 16, the length of the optical fiber 16 detoured by the first suspension portion 81 and the second suspension portion 82 is continuously shortened. Accordingly, the optical fiber 16 between the rear end of the inner needle 60 and the optical fiber fixing position 55b of the grip portion 55 maintains a state in which there is no slack and a large tension is not applied. This prevents the optical fiber 16 from being broken or damaged due to the injection of the inner needle 60, and prevents the optical fiber 16 from deviating from the first suspension portion 81 or the second suspension portion 82.

The situation in which the optical fiber 16 is broken or damaged as described above can occur similarly even in a case where the optical fiber is connected to the insertion needle for other purposes, such as lighting, for example, as disclosed in JP1995-54855Y (JP-H07-54855Y) as well as in a case where the optical fiber is connected to the insertion needle for photo acoustic imaging.

More specifically, the above-described detour length of the optical fiber 16 continuously changes with the movement of the inner needle 60 moves from a relatively long detour length, which absorbs the length of the optical fiber 16 corresponding to the inner needle injection distance (distance between the retracted position and the protruding position) and the above-described extra length in a case where the inner needle 60 is located at the retracted position, to a relatively short detour length, which absorbs only the extra length in a case where the inner needle 60 is located at the protruding position.

In addition, in a case where the inner needle 60 located at the protruding position is retracted, for example, by manual operation to return to the retracted position as described above, the pedestal 80 is biased by the above-described suspension portion biasing unit, such as a spring, to return to the position shown by the solid line in FIG. 4.

<Second Embodiment of an Insertion Device>

Figure 6:
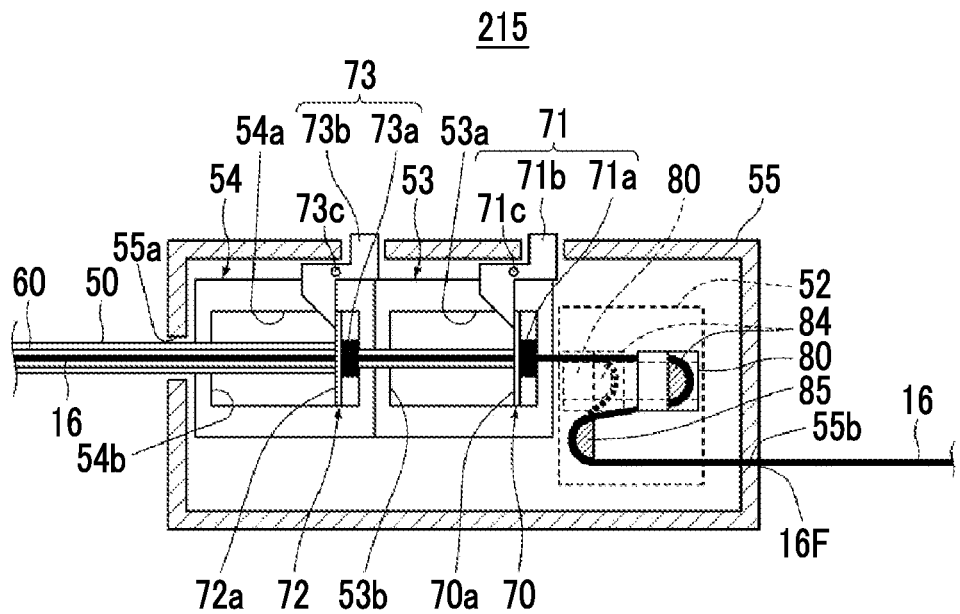
FIG. 6 is a partially broken side sectional view showing an insertion device according to a second embodiment of the present invention.
Figure 7:
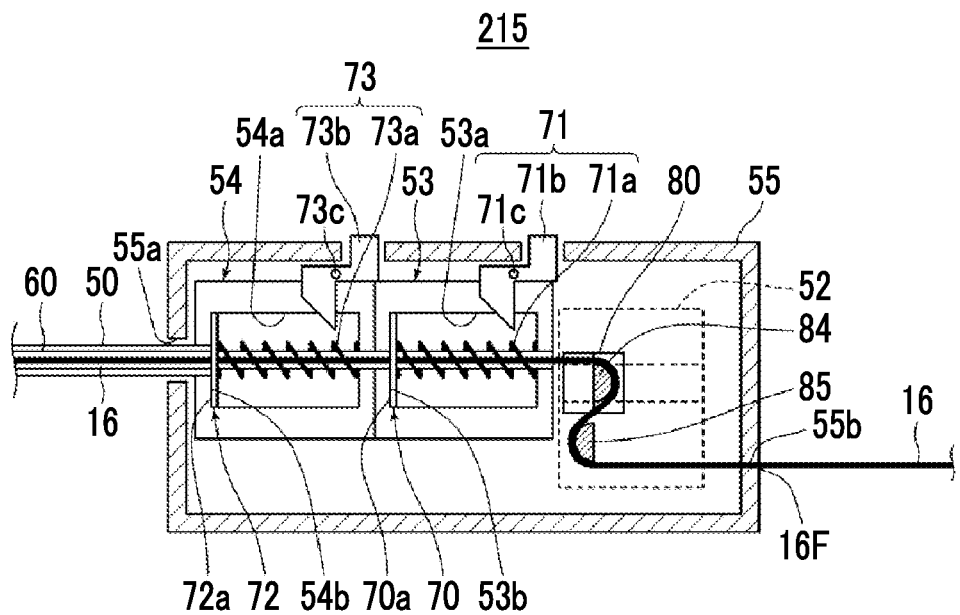
FIG. 7 is a partially broken side sectional view showing that the insertion device shown in FIG. 6 is in another state.

Next, an insertion device 215 according to a second embodiment of the present invention will be described with reference to FIGS. 6 and 7. FIG. 6 is a partially broken side view showing the insertion device 215 in a case where the outer needle 50 and the inner needle 60 are located at the above-described retracted position. On the other hand, FIG. 7 is a partially broken side view showing the insertion device 215 in a case where the outer needle 50 and the inner needle 60 are located at the above-described protruding position. In FIG. 6, the first suspension portion 81 in a case where the outer needle 50 and the inner needle 60 are located at the protruding position is also shown by a broken line. Also in the present embodiment, the optical fiber fixing position 55b of the grip portion 55 is the same position as the fixing portion 16F in the optical fiber 16.

The insertion device 215 of the present embodiment is different from the insertion device 15 of the first embodiment in that a first suspension portion 84 and a second suspension portion 85 for suspending the optical fiber 16 on a member having a convex curved surface are applied instead of the first suspension portion 81 and the second suspension portion 82 for suspending the optical fiber 16 on the rotating pulley. As the member described above, a cylindrical member or a member obtained by cutting a cylindrical member in a state in which a part of the circumferential surface is left is appropriately used. In the present embodiment, as an example of the latter member, a member having a shape obtained by cutting a cylindrical member in half by a plane including the central axis is used. It is preferable that such a member is a member with a small coefficient of friction of the convex curved surface. For example, such a member can be formed by using a synthetic resin appropriately.

In the present embodiment, the suspension portion linear driving unit for moving the first suspension portion 84 in the same direction as the injection direction of the inner needle 60 in conjunction with the injection operation of the inner needle 60 is configured to include the inner needle injection unit 71, the optical fiber 16 for transmitting the moving force of the inner needle 60 injected by the inner needle injection unit 71 to the first suspension portion 84, and the pedestal 80, in the same manner as in the first embodiment.

Also in the insertion device 215 of the present embodiment having the above-described configuration, the same effect as in the insertion device 15 of the first embodiment can be basically achieved.

Here, another example of the suspension portion linear driving unit will be described with reference to FIGS. 8 and 9. An insertion device 115 shown in the diagrams is a modification example of the insertion device 15 of the first embodiment, and the configuration of the insertion device 115 excluding a suspension portion linear driving unit, which will be described later, is basically the same as the configuration of the insertion device 15. A display method shown in FIGS. 8 and 9 is the same as that shown in FIGS. 4 and 5.

The suspension portion linear driving unit in this example is configured to include a movable base 90 that is movable in the movement direction of the inner needle 60, that is, in the horizontal direction in the diagrams in a state in which the first suspension portion 81 is mounted, a rod-shaped link member 91, the inner needle base 70, and the inner needle injection unit 71. The link member 91 forms a link mechanism together with the movable base 90, and has engaging pins 92 and 93 in the vicinity of the upper and lower ends, respectively. The upper engaging pin 92 is engaged with a connection portion (not shown) connected to the inner needle base 70. The lower engaging pin 93 is engaged with both a long hole 90a provided in the movable base 90 and a long hole 94 (shown by a broken line in the diagrams) drilled in a guide member (not shown) provided in the grip portion 55. The movable base 90 and the link member 91 form a link mechanism in the present invention. Also in this example, the optical fiber fixing position 55b of the grip portion 55 is the same position as the fixing portion 16F in the optical fiber 16.

Figure 8:
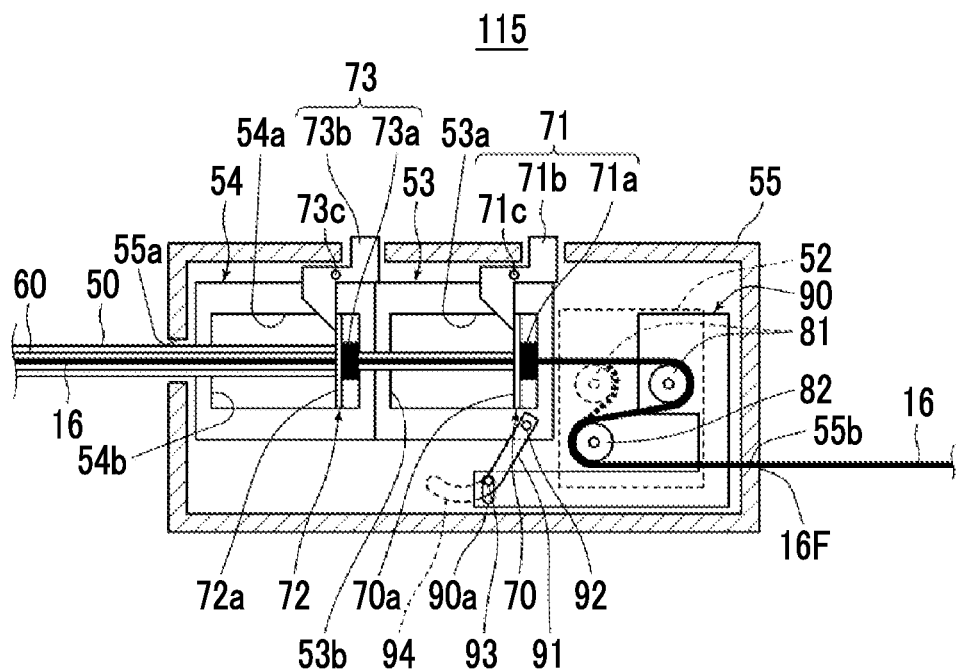
FIG. 8 is a partially broken side view showing an insertion device that is a modification example of the insertion device according to the first embodiment.
Figure 9:
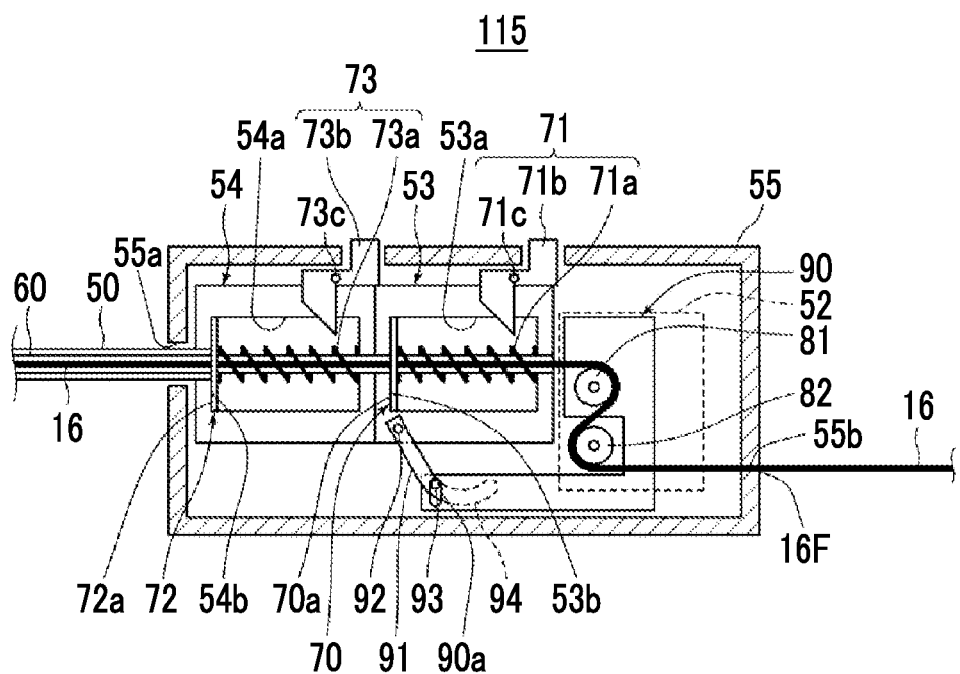
FIG. 9 is a partially broken side sectional view showing that the insertion device shown in FIG. 8 is in another state.

In the above configuration, the force with which the inner needle injection unit 71 injects the inner needle 60 from the state shown in FIG. 8 is transmitted from the portion of the engaging pin 92 to the link member 91 through the inner needle base 70 and the connection portion described above. As a result, the link member 91 moves forward together with the inner needle base 70, and moves the movable base 90 to the left in the diagram through the engaging pin 93. In this case, since the engaging pin 93 is engaged with the long hole 94, the amount of movement of the movable base 90 is also set to a predetermined value. In this manner, the first suspension portion 81 mounted in the movable base 90 moves from the position shown in FIG. 8 to the position shown in FIG. 9 in conjunction with the injection of the inner needle 60.

Next, still another example of the suspension portion linear driving unit will be described with reference to FIG. 10. The suspension portion linear driving unit in this example is configured to include a movable base 100 that is movable in the movement direction of the inner needle 60, that is, in the horizontal direction in the diagram in a state in which the first suspension portion 81 is mounted, a rack 101 that is attached upward to a portion in the vicinity of the front end of the movable base 100 and extends in a direction parallel to the movement direction of the inner needle 60, an inner needle base 170 having an L-shaped cross-section that is used instead of the inner needle base 70 shown in FIG. 9 and the like, a rack 102 that is attached downward to the bottom surface of the inner needle base 170 and extends in a direction parallel to the movement direction of the inner needle 60, a pinion (spur gear) 103 meshing with the rack 102, and a pinion 104 meshing with the pinion 103 and the rack 101.

Figure 10:
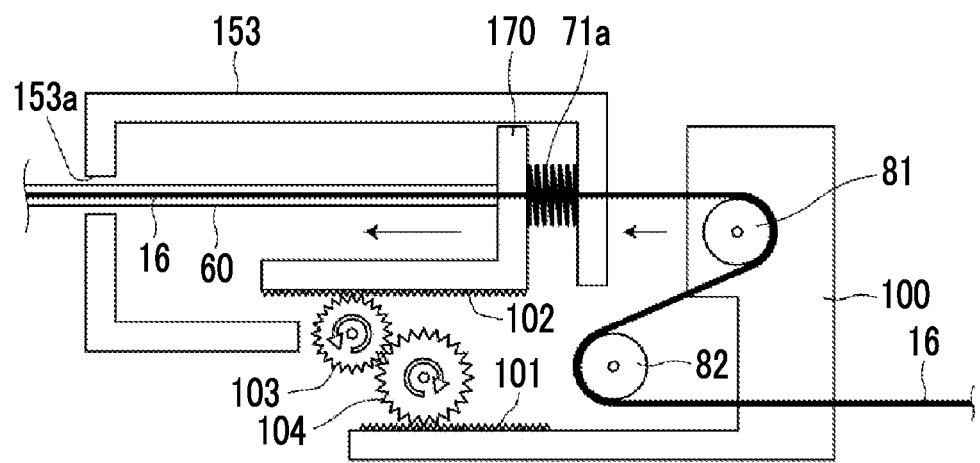
FIG. 10 is a side view showing another example of a suspension portion linear driving unit applied to the present invention.

In the above configuration, the force with which the coil spring 71a forming the inner needle injection unit injects the inner needle 60 in the state shown in FIG. 10 is transmitted to the movable base 100 through the inner needle base 170 and a gear mechanism configured to include the rack 102, the pinion 103, the pinion 104, and the rack 101. As a result, the movable base 100 moves forward, and the first suspension portion 81 mounted in the movable base 100 moves in the same direction as the inner needle injection direction from the position shown in FIG. 10 in conjunction with the injection of the inner needle 60.

In this example, since the first suspension portion 81 formed of a pulley acts as a movable pulley with respect to the optical fiber 16, the amount of movement of the movable base 100 in which the first suspension portion 81 is mounted needs to be ½ of the amount of movement of the inner needle base 170. Therefore, the ratio between the number of teeth of the pinion 103 and the number of teeth of the pinion 104 is set to 1:2.

<Third Embodiment of an Insertion Device>

Figure 11:
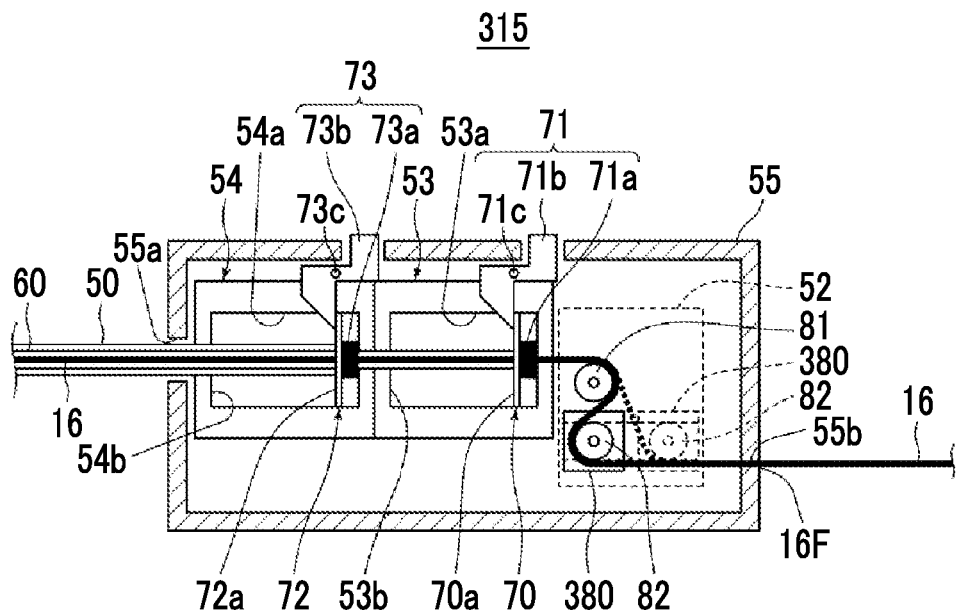
FIG. 11 is a partially broken side sectional view showing an insertion device according to a third embodiment of the present invention.
Figure 12:
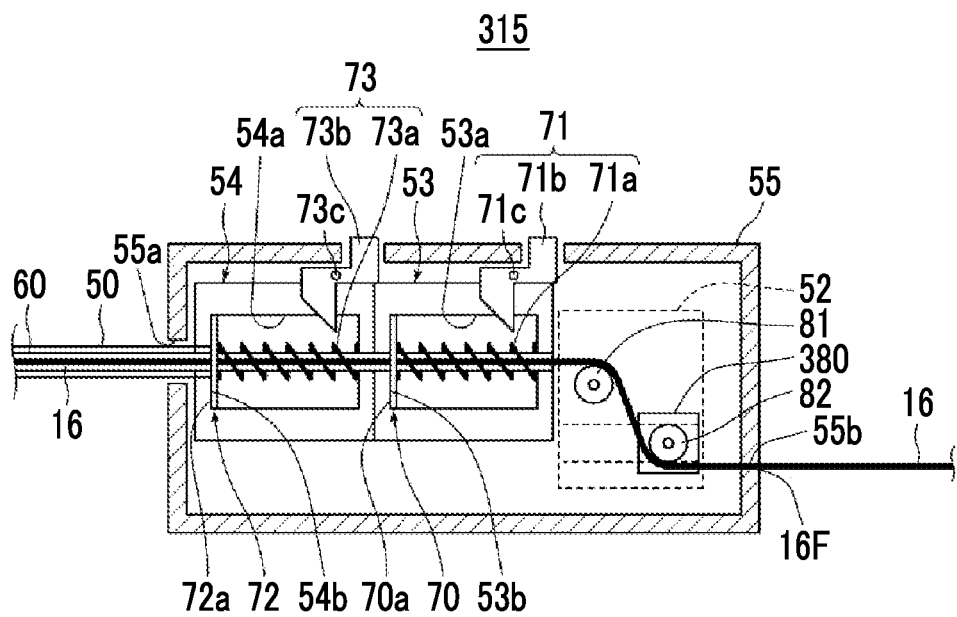
FIG. 12 is a partially broken side sectional view showing that the insertion device shown in FIG. 11 is in another state.

Next, an insertion device 315 according to a third embodiment of the present invention will be described with reference to FIGS. 11 and 12. FIG. 11 is a partially broken side view showing the insertion device 315 in a case where the outer needle 50 and the inner needle 60 are located at the above-described retracted position. On the other hand, FIG. 12 is a partially broken side view showing the insertion device 315 in a case where the outer needle 50 and the inner needle 60 are located at the above-described protruding position. In FIG. 11, the second suspension portion 82 in a case where the outer needle 50 and the inner needle 60 are located at the protruding position is also shown by a broken line.

The insertion device 315 of the present embodiment is different from the insertion device 15 of the first embodiment in that the second suspension portion 82 is moved instead of moving the first suspension portion 81 in conjunction with the injection of the inner needle 60. That is, in the present embodiment, a pedestal 380 is held by the fiber feeding adjustment mechanism 52 so as to be movable in the movement direction of the inner needle 60, that is, in the horizontal direction in the diagram, and the second suspension portion 82 formed of, for example, a pulley is held by the pedestal 380.

In the above configuration, the force with which the inner needle injection unit 71 injects the inner needle 60 from the state shown in FIG. 11 is transmitted to the pedestal 380 through, for example, a link mechanism (not shown). As a result, the pedestal 380 is moved in a direction opposite to the injection direction of the inner needle 60, that is, to the right in the diagram. Then, in a case where the inner needle 60 reaches the protruding position, the pedestal 380 and the second suspension portion 82 held by the pedestal 380 move to the position shown in FIG. 12. Specifically, as the link mechanism described above, it is possible to use a mechanism for switching the movement direction of the movable base 90 to a direction opposite to that shown in FIGS. 8 and 9 by interposing another link member between the movable base 90 and the link member 91 in the link mechanism shown in FIGS. 8 and 9. Instead of the link mechanism, it is also possible to use a gear mechanism. Specifically, as such a gear mechanism, it is possible to use a mechanism for switching the movement direction of the movable base 100 to a direction opposite to that shown in FIG. 10 by interposing another pinion between the two pinions 103 and 104 in the gear mechanism shown in FIG. 10.

In this manner, corresponding to the forward movement of the optical fiber 16, the length of the optical fiber 16 detoured by the first suspension portion 81 and the second suspension portion 82 is continuously shortened. Accordingly, the optical fiber 16 between the rear end of the inner needle 60 and the optical fiber fixing position 55b of the grip portion 55 maintains a state in which there is no slack and a large tension is not applied. This prevents the optical fiber 16 from being broken or damaged due to the injection of the inner needle 60, and prevents the optical fiber 16 from deviating from the first suspension portion 81 or the second suspension portion 82. Also in the present embodiment, the optical fiber fixing position 55b of the grip portion 55 is the same position as the fixing portion 16F in the optical fiber 16.

Also in the present embodiment, the above-described detour length of the optical fiber 16 continuously changes with the movement of the inner needle 60 moves from a relatively long detour length, which absorbs the length of the optical fiber 16 corresponding to the inner needle injection distance (distance between the retracted position and the protruding position) and the above-described extra length in a case where the inner needle 60 is located at the retracted position, to a relatively short detour length, which absorbs only the extra length in a case where the inner needle 60 is located at the protruding position.

<Fourth Embodiment of an Insertion Device>

Figure 13:
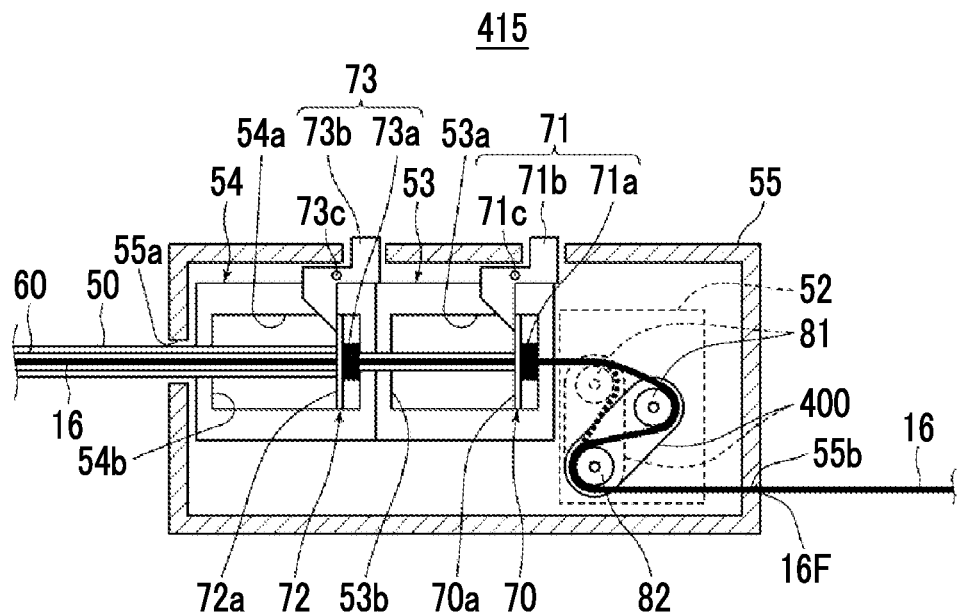
FIG. 13 is a partially broken side sectional view showing an insertion device according to a fourth embodiment of the present invention.
Figure 14:
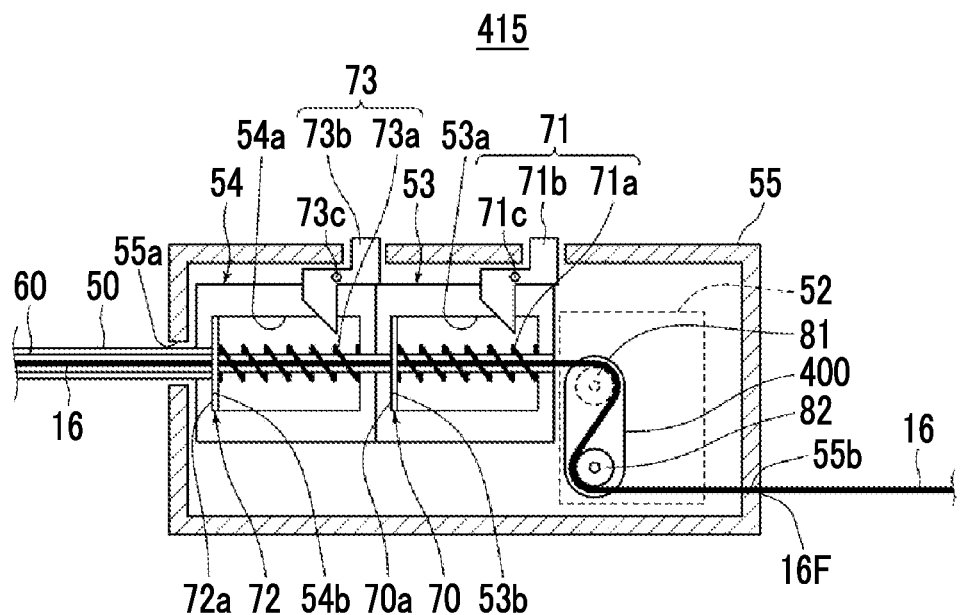
FIG. 14 is a partially broken side sectional view showing that the insertion device shown in FIG. 13 is in another state.

Next, an insertion device 415 according to a fourth embodiment of the present invention will be described with reference to FIGS. 13 and 14. FIG. 13 is a partially broken side view showing the insertion device 415 in a case where the outer needle 50 and the inner needle 60 are located at the above-described retracted position. On the other hand, FIG. 14 is a partially broken side view showing the insertion device 415 in a case where the outer needle 50 and the inner needle 60 are located at the above-described protruding position. In FIG. 13, the first suspension portion 81 in a case where the outer needle 50 and the inner needle 60 are located at the protruding position is also shown by a broken line.

The insertion device 415 of the present embodiment is different from the insertion device 15 of the first embodiment in that the first suspension portion 81 is rotated and moved instead of linearly moving the first suspension portion 81 in conjunction with the injection of the inner needle 60. That is, in the present embodiment, a rotating pedestal 400 that is rotatable while holding the first suspension portion 81 and the second suspension portion 82 is provided in the fiber feeding adjustment mechanism 52. The rotating pedestal 400 is rotatable around a shaft perpendicular to a surface (that is, one surface including the centerline of the optical fiber 16) on which the optical fiber 16 suspended on the suspension portions 81 and 82 extends. In the present embodiment, the above shaft matches a rotating shaft of a pulley forming the second suspension portion 82.

In the present embodiment, a suspension portion rotation driving unit in the present invention is configured to include the rotating pedestal 400, the inner needle injection unit 71, and a mechanism (not shown) for transmitting the moving force of the inner needle 60 injected by the inner needle injection unit 71 to the rotating pedestal 400. As the above mechanism, for example, a link mechanism or a gear mechanism can be used.

In the above configuration, the force with which the inner needle injection unit 71 injects the inner needle 60 from the state shown in FIG. 13 is transmitted to the rotating pedestal 400 through the above-described link mechanism or the like. As a result, the rotating pedestal 400 rotates counterclockwise in the diagram around the above-described shaft. Therefore, the first suspension portion 81 is rotated and moved in a direction approaching the inner needle 60 in conjunction with the injection operation of the inner needle 60. In a case where the inner needle 60 reaches the protruding position, the rotating pedestal 400 and the first suspension portion 81 held by the rotating pedestal 400 move to the position shown in FIG. 14.

In this manner, corresponding to the forward movement of the optical fiber 16, the length of the optical fiber 16 detoured by the first suspension portion 81 and the second suspension portion 82 is continuously shortened. Accordingly, the optical fiber 16 between the rear end of the inner needle 60 and the optical fiber fixing position 55b of the grip portion 55 maintains a state in which there is no slack and a large tension is not applied. This prevents the optical fiber 16 from being broken or damaged due to the injection of the inner needle 60, and prevents the optical fiber 16 from deviating from the first suspension portion 81 or the second suspension portion 82. Also in the present embodiment, the optical fiber fixing position 55b of the grip portion 55 is the same position as the fixing portion 16F in the optical fiber 16.

Also in the present embodiment, the above-described detour length of the optical fiber 16 continuously changes with the movement of the inner needle 60 moves from a relatively long detour length, which absorbs the length of the optical fiber 16 corresponding to the inner needle injection distance (distance between the retracted position and the protruding position) and the above-described extra length in a case where the inner needle 60 is located at the retracted position, to a relatively short detour length, which absorbs only the extra length in a case where the inner needle 60 is located at the protruding position.

<Fifth Embodiment of an Insertion Device>

Figure 15:
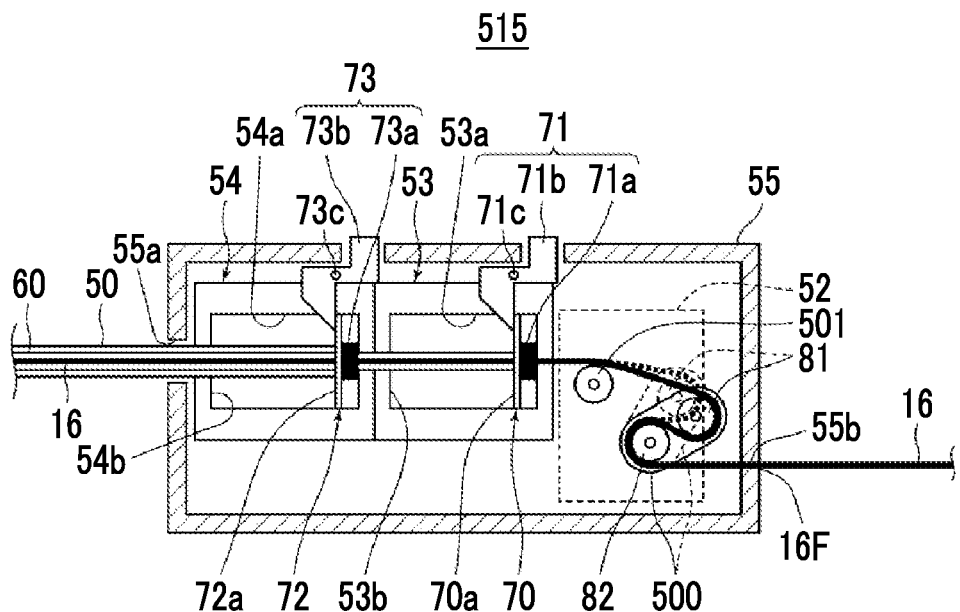
FIG. 15 is a partially broken side sectional view showing an insertion device according to a fifth embodiment of the present invention.
Figure 16:
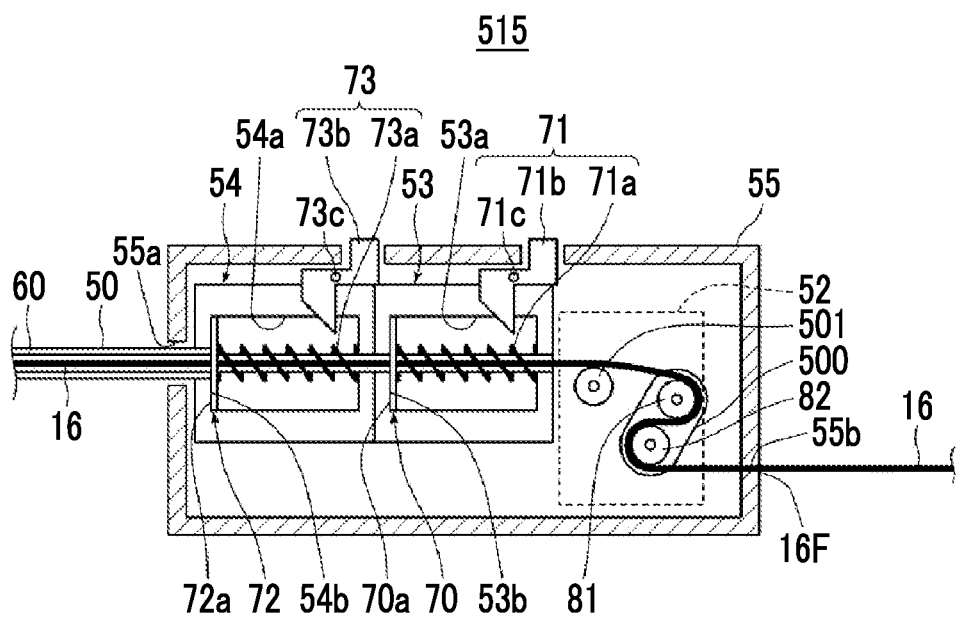
FIG. 16 is a partially broken side sectional view showing that the insertion device shown in FIG. 15 is in another state.

Next, an insertion device 515 according to a fifth embodiment of the present invention will be described with reference to FIGS. 15 and 16. FIG. 15 is a partially broken side view showing the insertion device 515 in a case where the outer needle 50 and the inner needle 60 are located at the above-described retracted position. On the other hand, FIG. 16 is a partially broken side view showing the insertion device 515 in a case where the outer needle 50 and the inner needle 60 are located at the above-described protruding position. In FIG. 15, the first suspension portion 81 in a case where the outer needle 50 and the inner needle 60 are located at the protruding position is also shown by a broken line.

The insertion device 515 of the present embodiment is different from the insertion device 415 of the fourth embodiment in that a rotating pedestal 500 is used instead of the rotating pedestal 400 and a guide pulley 501 is further provided. The guide pulley 501 is provided between the rear end of the inner needle 60 and the first suspension portion 81, thereby forming guide unit for changing the extension direction of the optical fiber 16. Also in the present embodiment, the optical fiber fixing position 55b of the grip portion 55 is the same position as the fixing portion 16F in the optical fiber 16.

The rotating pedestal 500 rotates in the same manner as the rotating pedestal 400 in the fourth embodiment. Therefore, also in the present embodiment, basically the same effect as in the fourth embodiment can be achieved. In addition, in the present embodiment, by providing the guide pulley 501 as described above, it is possible to increase the degree of freedom of the arrangement of the rotating pedestal 500, that is, the degree of freedom of the arrangement of the first suspension portion 81 and the second suspension portion 82.

Although the embodiments applied to the insertion needle unit in which the outer needle 50 and the inner needle 60 are combined have been described above, the present invention is not limited to such an insertion needle, but can be applied to an insertion device having one insertion needle.

In addition, the insertion needle forming the insertion device is not limited to the biopsy needle for sampling, but may be an insertion needle for performing other treatments, such as medical treatment or chemical injection, for the subject.

Figure 17:
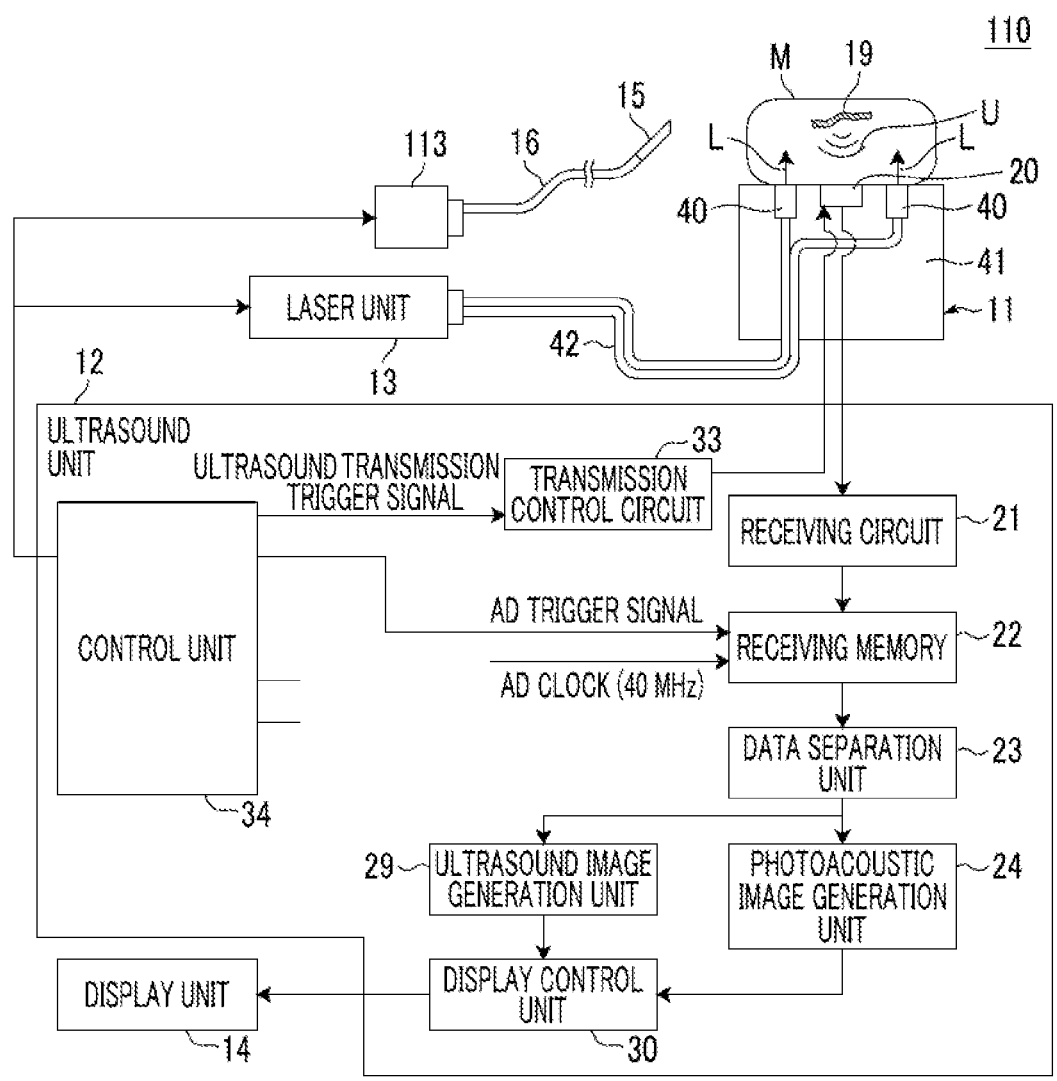
FIG. 17 is a schematic diagram showing the overall configuration of a photoacoustic measurement apparatus according to another embodiment of the present invention.

Here, another embodiment of the photoacoustic measurement apparatus will be described. A photoacoustic measurement apparatus 110 shown in FIG. 17 is different from the photoacoustic measurement apparatus 10 shown in FIG. 1 in that not only the relatively high-output laser unit 13 that transmits the laser light L to the probe 11 in order to acquire a photoacoustic image of the subject M but also another laser unit 113 is provided. As the laser unit 113, for example, a relatively low-output laser light source, such as a laser diode (LD) or a light emitting diode (LED), can be applied. This is because the attenuation of light is small compared with a case of emitting the laser light L from a body surface affected by absorption and scattering in the tissue in order to guide light to the insertion needle distal end using an optical fiber. In this example, the driving of the laser unit 113 is controlled by the control unit 34 that controls the driving of the laser unit 13. However, the present invention is not limited thereto, and the driving of the laser unit 113 may be controlled by another control unit other than the control unit 34.

The laser light emitted from the laser unit 113 is guided by the optical fiber 16 and is transmitted to the insertion device 15. Also in this case, a part of the optical fiber 16 forms the insertion device 15. In the present embodiment, as an insertion device, the insertion device 15 of the first embodiment described above is used. However, the insertion device according to any of the first to fifth embodiments may be applied.

Thus, in a case where different light sources, that is, the laser unit 13 and the laser unit 113 are used for acquisition of a photoacoustic image showing blood vessels and the like in the subject M and acquisition of a photoacoustic image showing an insertion needle distal end portion, these light sources can be driven independently of each other. In this case, therefore, the photoacoustic image and the ultrasound image of the subject M and the photoacoustic image of the insertion needle can be separately acquired and displayed. In a case where the photoacoustic image of the subject M and a portion in the vicinity of the distal end of the inner needle 60 are displayed together on the display unit 14, it is also possible to separately display the tissue, such as a blood vessel, and the portion in the vicinity of the inner needle distal end in different colors. Since the tissue, such as a blood vessel, and the portion in the vicinity of the inner needle distal end can be more clearly distinguished and recognized, it is possible to safely collect a sample with the inner needle 60 while avoiding the tissue, such as a blood vessel.

Also in a case where only one light source, such as a laser unit, is provided as in FIG. 1, light emitted from the light source is branched into two optical paths, and a shutter is provided in each optical path. In a case where the light is selectively transmitted to either the probe 11 or the insertion device 15 by opening and closing these shutters, a photoacoustic wave detection signal relevant to the former photoacoustic image and a photoacoustic wave detection signal relevant to the latter photoacoustic image can be alternately acquired by switching the opening and closing state of the two shutters within a short period of time. Therefore, the same effect can be obtained.

Figure 18:
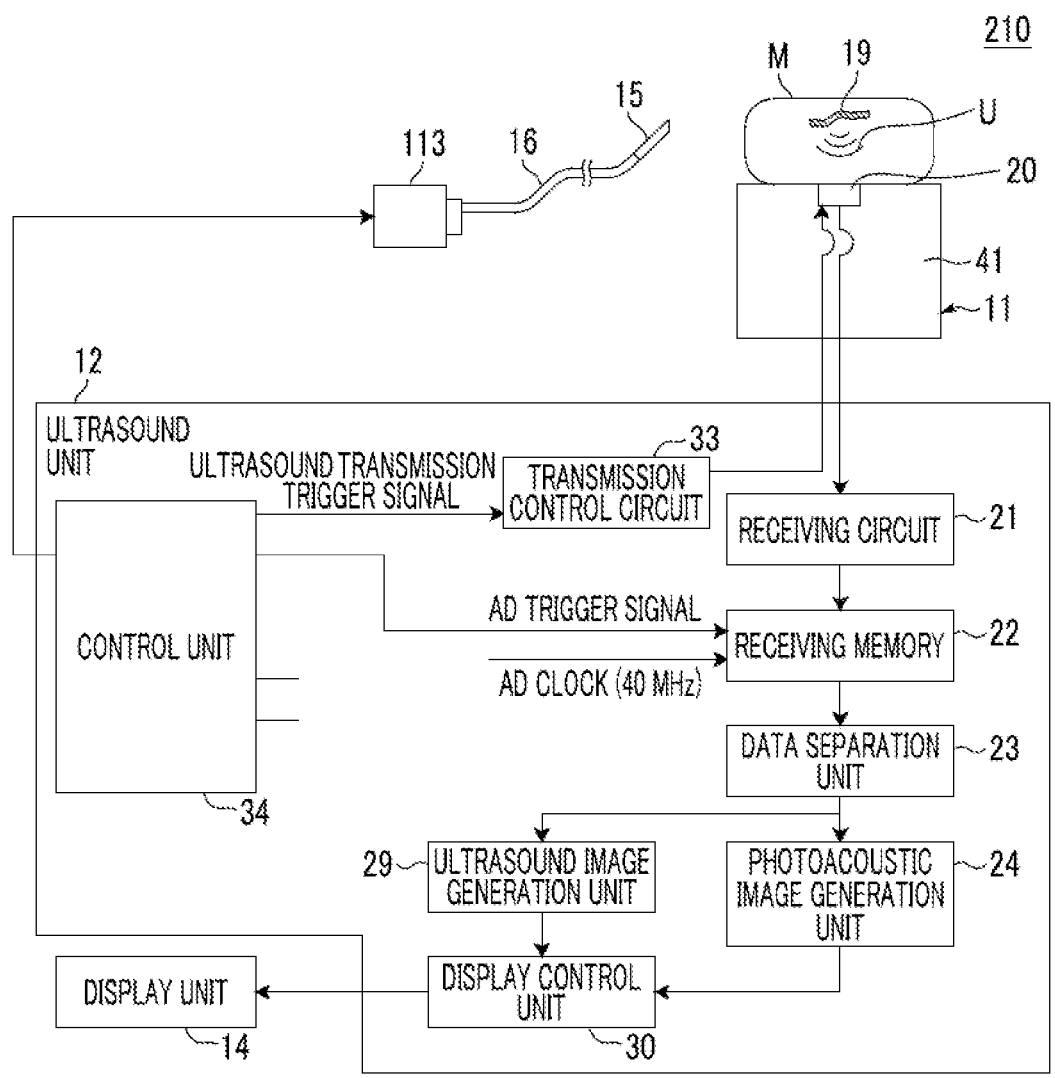
FIG. 18 is a schematic diagram showing the overall configuration of a photoacoustic measurement apparatus according to still another embodiment of the present invention.

Next, still another embodiment of the photoacoustic measurement apparatus will be described. A photoacoustic measurement apparatus 210 shown in FIG. 18 is different from the photoacoustic measurement apparatus 110 shown in FIG. 17 in that a configuration for acquiring a photoacoustic image of the subject M, that is, the laser unit 13, the optical fiber 42, and the light emitting unit 40, are omitted. That is, the probe 11 in the present embodiment does not have a light emission function.

According to such a photoacoustic measurement apparatus 210, an ultrasound image of the subject M and a photoacoustic image of the insertion needle are acquired, and a photoacoustic image showing the vicinity of the distal end of the inner needle 60 (refer to FIG. 4) of the insertion device 15 is displayed on the display unit 14 so as to overlap the ultrasound image of the subject M.

Since the photoacoustic measurement apparatus 210 having the above-described configuration can be formed simply by adding the insertion device 15, the laser unit 113, and program software for photoacoustic image acquisition to the existing ultrasound image acquisition apparatus, it is possible to cope with the request for checking the distal end of the insertion needle at low cost.

EXPLANATION OF REFERENCES 10, 110, 210: photoacoustic measurement apparatus
11: probe
12: ultrasound unit
13: laser unit
14: display unit
15, 115, 215, 315, 415, 515: insertion device
16: optical fiber
16F: fixing portion of optical fiber
20: transducer array
21: receiving circuit
22: receiving memory
23: data separation unit
24: photoacoustic image generation unit
29: ultrasound image generation unit
30: display control unit
33: transmission control circuit
34: control unit
40: light emitting unit
50: outer needle
51: distal end of an outer needle
52: fiber feeding adjustment mechanism
53: inner needle holding portion
53a: inner needle guide portion
53b: front wall of inner needle holding portion
54: outer needle holding portion
54a: outer needle guide portion
54b: front wall of outer needle holding portion
55: grip portion
55a: opening of a grip portion
55b: optical fiber fixing position of a grip portion
60: inner needle
61: distal end of an inner needle
62: sample collection portion
64: light absorber
70: inner needle base
71: inner needle injection unit
71a, 73a: coil spring
71b, 73b: trigger member
72: outer needle base
73: outer needle injection unit
80, 380: pedestal 81, 84: first suspension portion
82, 85: second suspension portion
90, 100: movable base
91: link member
101, 102: rack
103, 104: pinion
400, 500: rotating pedestal
501: guide pulley (guide unit)
L: laser light
M: subject
U: acoustic wave

What is claimed is:

1. An insertion device, comprising:
an insertion needle that is inserted into a subject from a distal end;
a grip portion that holds the insertion needle so as to be movable in an axis direction of the insertion needle;
a needle injection unit for injecting the insertion needle from a retracted position to a protruding position away from the retracted position toward a distal end side of the insertion needle by a predetermined injection distance; and
an optical fiber that is disposed in the insertion needle to guide light from a rear end of the insertion needle,
wherein the optical fiber is fixed to the grip portion at a fixing portion that is separated from the rear end of the insertion needle to the other end side of the optical fiber, and
a fiber feeding adjustment mechanism is provided that suspends the optical fiber between the rear end of the insertion needle and the fixing portion in the grip portion so as to make a detour in a state in which there is no slack and changes a detour length continuously according to movement of the insertion needle in a case where the insertion needle moves between the retracted position and the protruding position, thereby maintaining a state in which the optical fiber is suspended without slack.

2. The insertion device according to claim 1,
wherein the fiber feeding adjustment mechanism is configured to include:
a first suspension portion that suspends the optical fiber extending rearward from the rear end of the insertion needle to change an extension direction of the optical fiber;
a second suspension portion that suspends the optical fiber having passed through the first suspension portion to guide the optical fiber rearward; and
a suspension portion linear driving unit for moving the first suspension portion in the same direction as an injection direction of the insertion needle in conjunction with an injection operation of the insertion needle.

3. The insertion device according to claim 2,
wherein the suspension portion linear driving unit is configured to include the needle injection unit and the optical fiber for transmitting a moving force of the insertion needle injected by the needle injection unit to the first suspension portion.

4. The insertion device according to claim 3, further comprising:
a suspension portion biasing unit for biasing the first suspension portion in a direction opposite to the injection direction of the insertion needle.

5. The insertion device according to claim 3, further comprising:
a contact portion that is in contact with the moving first suspension portion to define a maximum movement distance of the first suspension portion.

6. The insertion device according to claim 2,
wherein the suspension portion linear driving unit is configured to include the needle injection unit and a link mechanism for transmitting a moving force of the insertion needle injected by the needle injection unit to the first suspension portion.

7. The insertion device according to claim 2,
wherein the suspension portion linear driving unit is configured to include the needle injection unit and a gear mechanism for transmitting a moving force of the insertion needle injected by the needle injection unit to the first suspension portion.

8. The insertion device according to claim 1,
wherein the fiber feeding adjustment mechanism is configured to include:
a first suspension portion that suspends the optical fiber extending rearward from the rear end of the insertion needle to change an extension direction of the optical fiber;
a second suspension portion that suspends the optical fiber having passed through the first suspension portion to guide the optical fiber rearward; and
a suspension portion linear driving unit for moving the second suspension portion in a direction opposite to an injection direction of the insertion needle in conjunction with an injection operation of the insertion needle.

9. The insertion device according to claim 8,
wherein the suspension portion linear driving unit is configured to include the needle injection unit and a link mechanism for transmitting a moving force of the insertion needle injected by the needle injection unit to the second suspension portion.

10. The insertion device according to claim 8,
wherein the suspension portion linear driving unit is configured to include the needle injection unit and a gear mechanism for transmitting a moving force of the insertion needle injected by the needle injection unit to the second suspension portion.

11. The insertion device according to claim 2,
wherein the first and second suspension portions are disposed so as to suspend the optical fiber in an S shape.

12. The insertion device according to claim 1,
wherein the fiber feeding adjustment mechanism is configured to include:
a first suspension portion that suspends the optical fiber extending rearward from the rear end of the insertion needle to change an extension direction of the optical fiber;
a second suspension portion that suspends the optical fiber having passed through the first suspension portion to guide the optical fiber rearward;
a rotating pedestal that is rotatable around a shaft perpendicular to a surface, on which the optical fiber suspended on the first suspension portion and the second suspension portion extends, while holding the first and second suspension portions; and
a suspension portion rotation driving unit for rotating the rotating pedestal in a direction, in which the first suspension portion approaches the insertion needle, in conjunction with an injection operation of the insertion needle.

13. The insertion device according to claim 12,
wherein the suspension portion rotation driving unit is configured to include the needle injection unit and a link mechanism for transmitting a moving force of the insertion needle injected by the needle injection unit to the rotating pedestal.

14. The insertion device according to claim 12,
wherein the suspension portion rotation driving unit is configured to include the needle injection unit and a gear mechanism for transmitting a moving force of the insertion needle injected by the needle injection unit to the rotating pedestal.

15. The insertion device according to claim 2,
wherein at least one of the first suspension portion or the second suspension portion has a configuration in which the optical fiber is suspended on a pulley.

16. The insertion device according to claim 2,
wherein at least one of the first suspension portion or the second suspension portion has a configuration in which the optical fiber is suspended on a member having a convex curved surface for sliding the optical fiber.

17. The insertion device according to claim 2, further comprising:
a guide unit for changing the extension direction of the optical fiber, the guide unit being located between the rear end of the insertion needle and the first suspension portion.

18. The insertion device according to claim 1,
wherein the rear end of the insertion needle is fixed to a base, and the insertion needle is injected through the base.

19. The insertion device according to claim 1,
wherein the needle injection unit injects the insertion needle with a spring force.

20. The insertion device according to claim 1,
wherein the insertion needle is a biopsy needle having a recessed sample collection portion cut inward from an outer peripheral surface.

21. The insertion device according to claim 1,
wherein the insertion needle is an inner needle in an insertion needle unit having a hollow tubular outer needle and an inner needle that is housed in the outer needle and is movable in a tube axis direction of the outer needle.

22. The insertion device according to claim 21, further comprising:
an outer needle injection unit for injecting the outer needle in the same direction as an injection direction of the inner needle that is the insertion needle.

23. A photoacoustic measurement apparatus, comprising:
the insertion device according to claim 1.

* * * * *